US 10,188,307 B2

(12) United States Patent
Henson et al.

(10) Patent No.: US 10,188,307 B2
(45) Date of Patent: Jan. 29, 2019

(54) SHIELDED MULTI-CHANNEL EEG HEADSET SYSTEMS AND METHODS

(71) Applicant: Bio-Signal Group Corp., Brooklyn, NY (US)

(72) Inventors: James C. Henson, New York, NY (US); Anderson Micu, Somerset, NJ (US); Samah Abdel Baki, Brooklyn, NY (US)

(73) Assignee: Bio-Signal Group Corp., Brooklyn, NY (US)

( * ) Notice: Subject to any disclaimer, the term of this patent is extended or adjusted under 35 U.S.C. 154(b) by 1120 days.

(21) Appl. No.: 14/378,498

(22) PCT Filed: Feb. 22, 2013

(86) PCT No.: PCT/US2013/027464
§ 371 (c)(1),
(2) Date: Aug. 13, 2014

(87) PCT Pub. No.: WO2013/126798
PCT Pub. Date: Aug. 29, 2013

(65) Prior Publication Data
US 2015/0011857 A1  Jan. 8, 2015

Related U.S. Application Data

(60) Provisional application No. 61/602,292, filed on Feb. 23, 2012.

(51) Int. Cl.
*A61B 5/0478* (2006.01)
*A61B 5/00* (2006.01)
*B32B 37/24* (2006.01)

(52) U.S. Cl.
CPC .......... *A61B 5/0478* (2013.01); *A61B 5/6803* (2013.01); *A61B 5/6814* (2013.01);
(Continued)

(58) Field of Classification Search
CPC .................................................... A61B 5/0478
(Continued)

(56) References Cited

U.S. PATENT DOCUMENTS 1,968,767 A   7/1934  Howard
3,942,517 A   3/1976  Bowles
(Continued)

FOREIGN PATENT DOCUMENTS

WO   WO-2004000115 A1   12/2003
WO   WO-20080109694 A1   9/2008
(Continued)

OTHER PUBLICATIONS

"U.S. Appl. No. 13/284,886, Advisory Action dated Jun. 19, 2015", 3 pgs.
(Continued)

*Primary Examiner* — Lee S Cohen
(74) *Attorney, Agent, or Firm* — Schwegman Lundberg & Woessner, P.A.

(57) ABSTRACT

Embodiments of a shielded sensor headset including a plurality of electrodes are generally described herein. In some embodiments a sensor headset can include electrodes, traces, and connection terminals printed on a first side of a flexible insulating substrate; and a shield plane printed on a second side of the flexible insulating substrate, the shield plane providing protection against interference. In some embodiments a sensor headset can include a first and a second assembly each having a plurality of electrodes, the first and second assemblies being configured to mate such that the electrodes comply with the 10-20 standard for EEG electrode placement. In some embodiments a sensor headset can include a dual-layer foam reservoir disposed above individual electrodes. An inner layer of the dual-layer foam reservoir can be in contact with an electrode, include a (Continued)

conductive gel, and form a cavity for receiving additional gel through a perforation in the electrode.

19 Claims, 21 Drawing Sheets

(52) U.S. Cl.
CPC ............ *A61B 5/6831* (2013.01); *B32B 37/24* (2013.01); *A61B 2562/125* (2013.01); *A61B 2562/164* (2013.01); *A61B 2562/182* (2013.01); *A61B 2562/222* (2013.01); *B32B 2037/243* (2013.01); *B32B 2255/00* (2013.01); *B32B 2307/202* (2013.01); *B32B 2307/204* (2013.01)

(58) Field of Classification Search
USPC .......................................................... 600/383
See application file for complete search history.

(56) References Cited

U.S. PATENT DOCUMENTS

| | | | |
|---|---|---|---|
| 3,998,213 | A | 12/1976 | Price |
| 4,085,739 | A | 4/1978 | Sams |
| 4,257,424 | A | 3/1981 | Cartmell |
| 4,323,076 | A | 4/1982 | Sams |
| 4,353,372 | A | 10/1982 | Ayer |
| D277,787 | S | 2/1985 | Corbett |
| 4,537,198 | A | 8/1985 | Corbett |
| 4,683,892 | A | 8/1987 | Johansson et al. |
| 4,709,702 | A | 12/1987 | Sherwin |
| 4,967,038 | A | 10/1990 | Gevins et al. |
| 5,119,816 | A | 6/1992 | Gevins |
| 5,222,503 | A | 6/1993 | Ives et al. |
| 5,273,037 | A | 12/1993 | Itil et al. |
| 5,275,172 | A | 1/1994 | Ives |
| 5,293,867 | A | 3/1994 | Oommen |
| 5,357,957 | A | 10/1994 | Itil et al. |
| 5,415,282 | A | 5/1995 | Kienholz |
| 5,445,162 | A | 8/1995 | Ives |
| 5,479,934 | A | 1/1996 | Imran |
| 5,660,177 | A | 8/1997 | Faupel et al. |
| 5,772,591 | A | 6/1998 | Cram |
| 5,800,351 | A | 9/1998 | Mann |
| 5,813,993 | A | 9/1998 | Kaplan et al. |
| 5,817,029 | A | 10/1998 | Gevins et al. |
| 6,032,064 | A | 2/2000 | Devlin et al. |
| 6,032,065 | A | 2/2000 | Brown |
| 6,067,464 | A | 5/2000 | Musha |
| 6,154,669 | A | 11/2000 | Hunter et al. |
| 6,161,030 | A | 12/2000 | Levendowski et al. |
| 6,175,753 | B1 | 1/2001 | Menkes et al. |
| 6,198,958 | B1 | 3/2001 | Ives et al. |
| 6,201,982 | B1 | 3/2001 | Menkes et al. |
| 6,266,556 | B1 | 7/2001 | Ives et al. |
| 6,289,238 | B1 | 9/2001 | Besson et al. |
| 6,301,493 | B1 | 10/2001 | Marro et al. |
| 6,381,481 | B1 | 4/2002 | Levendowski et al. |
| 6,383,143 | B1 | 5/2002 | Rost |
| 6,394,953 | B1 | 5/2002 | Devlin et al. |
| 6,510,340 | B1 | 1/2003 | Jordan |
| 6,571,123 | B2 | 5/2003 | Ives et al. |
| 6,574,513 | B1 | 6/2003 | Collura et al. |
| 6,577,893 | B1 | 6/2003 | Besson et al. |
| 6,640,122 | B2 | 10/2003 | Manoli et al. |
| 6,654,626 | B2 | 11/2003 | Devlin et al. |
| 6,708,051 | B1 | 3/2004 | Durousseau |
| 7,054,681 | B2 | 5/2006 | Husar et al. |
| 7,551,952 | B2 | 6/2009 | Gevins et al. |
| 7,835,787 | B2 | 11/2010 | Sajda et al. |
| 7,885,706 | B2 | 2/2011 | Ludvig et al. |
| 8,019,402 | B1 | 9/2011 | Kryzpow et al. |
| 8,065,796 | B2 | 11/2011 | Curry |
| 9,408,575 | B2 | 8/2016 | Bordoley et al. |
| 2001/0044573 | A1 | 11/2001 | Manoli et al. |
| 2002/0019588 | A1 | 2/2002 | Marro et al. |
| 2002/0072685 | A1 | 6/2002 | Rymut et al. |
| 2002/0183605 | A1 | 12/2002 | Devlin et al. |
| 2002/0188216 | A1 | 12/2002 | Kayyali |
| 2003/0038047 | A1 | 2/2003 | Sleva et al. |
| 2003/0144600 | A1 | 7/2003 | Yarita |
| 2004/0030258 | A1 | 2/2004 | Williams et al. |
| 2005/0054941 | A1 | 3/2005 | Ting et al. |
| 2005/0113666 | A1 | 5/2005 | Bonmassar et al. |
| 2005/0137472 | A1 | 6/2005 | Ryu et al. |
| 2005/0197556 | A1 | 9/2005 | Stoler |
| 2005/0247319 | A1 | 11/2005 | Berger |
| 2005/0277819 | A1 | 12/2005 | Kiani et al. |
| 2006/0161058 | A1 | 7/2006 | Ives et al. |
| 2006/0161072 | A1 | 7/2006 | Mase et al. |
| 2007/0038382 | A1 | 2/2007 | Keenan |
| 2007/0055169 | A1 | 3/2007 | Lee et al. |
| 2007/0173699 | A1 | 7/2007 | Mathan et al. |
| 2007/0235716 | A1 | 10/2007 | Delic et al. |
| 2007/0238945 | A1 | 10/2007 | Delic et al. |
| 2008/0027345 | A1 | 1/2008 | Kumada et al. |
| 2008/0082019 | A1 | 4/2008 | Ludving et al. |
| 2008/0146958 | A1 | 6/2008 | Guillory et al. |
| 2008/0226255 | A1 | 9/2008 | Estes |
| 2008/0306397 | A1 | 12/2008 | Bonmassar et al. |
| 2009/0105576 | A1 | 4/2009 | Do et al. |
| 2009/0105577 | A1 | 4/2009 | Wu et al. |
| 2009/0281446 | A2 | 11/2009 | Ludvig Nandor et al. |
| 2009/0326404 | A1 | 12/2009 | Sajda et al. |
| 2010/0036275 | A1 | 2/2010 | Alkire |
| 2010/0041962 | A1 | 2/2010 | Causevic et al. |
| 2010/0274152 | A1 | 10/2010 | McPeck et al. |
| 2011/0004089 | A1 | 1/2011 | Chou |
| 2011/0015503 | A1 | 1/2011 | Joffe et al. |
| 2011/0144522 | A1 | 6/2011 | Sajda et al. |
| 2011/0270117 | A1 | 11/2011 | Warwick et al. |
| 2011/0282231 | A1 | 11/2011 | Pradeep et al. |
| 2012/0143020 | A1 | 6/2012 | Bordoley et al. |

FOREIGN PATENT DOCUMENTS

| | | |
|---|---|---|
| WO | WO-2010129026 A2 | 11/2010 |
| WO | WO-2010129026 A3 | 2/2011 |
| WO | WO-2013126798 A2 | 8/2013 |
| WO | WO-2013126798 A3 | 8/2013 |

OTHER PUBLICATIONS

"U.S. Appl. No. 13/284,886, Non Final Office Action dated Nov. 6, 2015", 11 pgs.
"U.S. Appl. No. 13/284,886, Response to Non Final Office Action dated Nov. 6, 2015", 10 pgs.
"U.S. Appl. No. 13/284,886, Notice of Allowance dated Apr. 11, 2016", 11 pgs.
"501(k) Summary (K010460)", Lifelines Ltd., FDA Approval Date: May 14, 2001, 177 pgs.
"501(k) Summary (K042039)", Cleveland Medical Devices, Inc., FDA Approval Date: Nov. 17, 2004, 170 pgs.
"Electro-Cap International, Inc.", http://www.electro-cap.com/caps.htm, [website visited Apr. 28, 2010], 2 pgs.
"HydroCel Geodesic Sensor Nets", http://www.egi.com/research-division-research-products/sensor-nets, [website visited Apr. 28, 2010], 2 pgs.
"International Application Serial No. PCT/US2010/001264, International Preliminary Report on Patentability dated Aug. 24, 2011", 19 pgs.
"International Application Serial No. PCT/US2010/001264, Invitation to Pay Additional Fee dated Aug. 17, 2010", 7 pgs.
"International Application Serial No. PCT/US2010/001264, Search Report dated Dec. 13, 2010", 7 pgs.
"International Application Serial No. PCT/US2010/001264, Written Opinion dated Dec. 13, 2010", 10 pgs.
"International Application Serial No. PCT/US2013/027464, International Search Report dated Oct. 7, 2013", 6 pgs.

(56) References Cited

OTHER PUBLICATIONS

"International Application Serial No. PCT/US2013/027464, Invitation to Pay Additional Fees and Partial Search Report dated Jun. 18, 2013", 7 pgs.

"International Application Serial No. PCT/US2013/027464, Written Opinion dated Oct. 7, 2013", 11 pgs.

Fenton, A. A., et al., "A Step Toward Routine EEG Recording in the Emergency Department", BioSignal, poster presentation, (Dec. 6, 2009), 1 pg.

Omurtag, Ahmet, et al., "BioSignal Grant Application", grant application submission date was Sep. 1, 2009, 138 pgs.

"U.S. Appl. No. 13/284,886, Final Office Action dated Apr. 7, 2015", 22 pgs.

"U.S. Appl. No. 13/284,886, Non Final Office Action dated Sep. 17, 2014", 21 pgs.

"U.S. Appl. No. 13/284,886, Response filed Jun. 8, 2015 to Final Office Action dated Apr. 7, 2015", 12 pgs.

"U.S. Appl. No. 13/284,886, Response filed Dec. 17, 2014 to Non Final Office Action dated Sep. 17, 2014", 13 pgs.

"International Application Serial No. PCT/US2013/027464, International Preliminary Report on Patentability dated Sep. 4, 2014", 13 pgs.

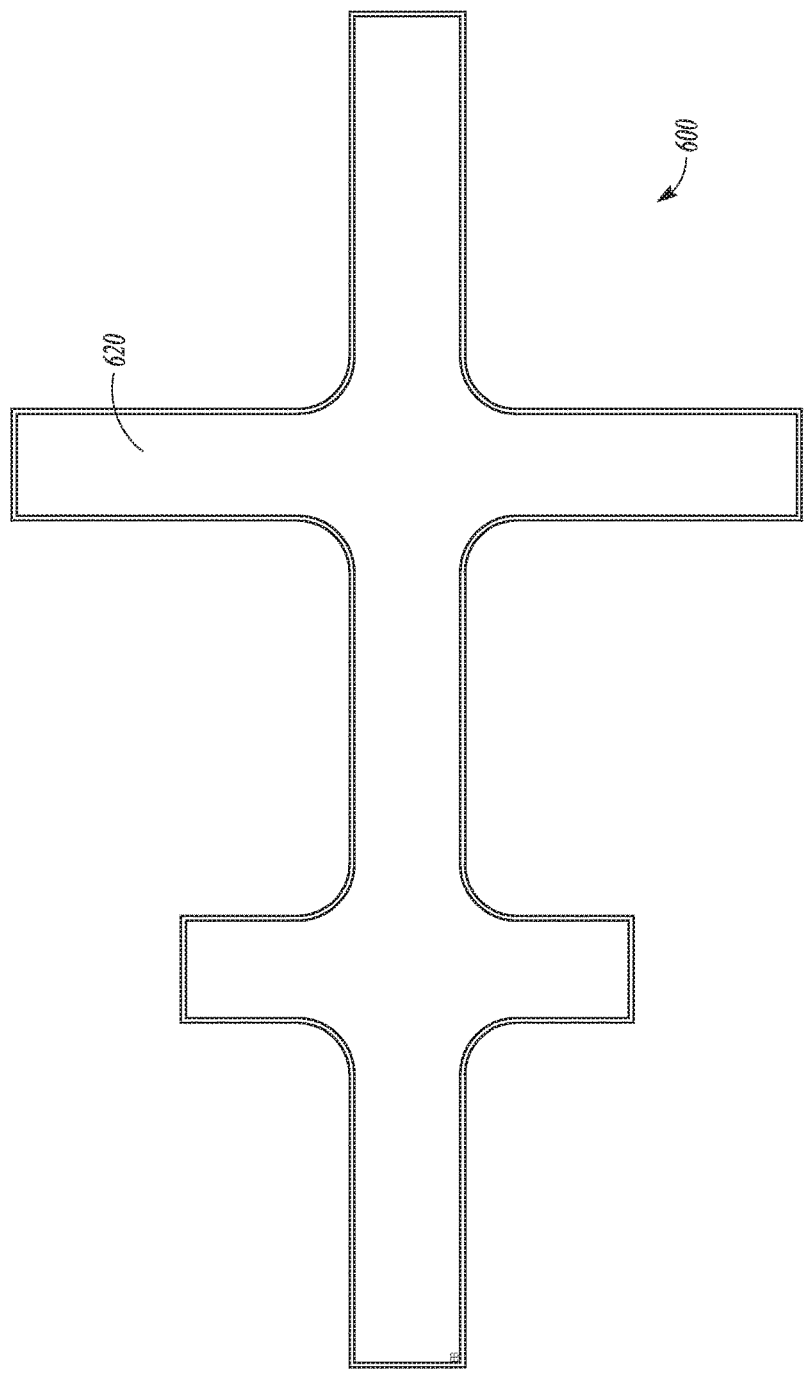

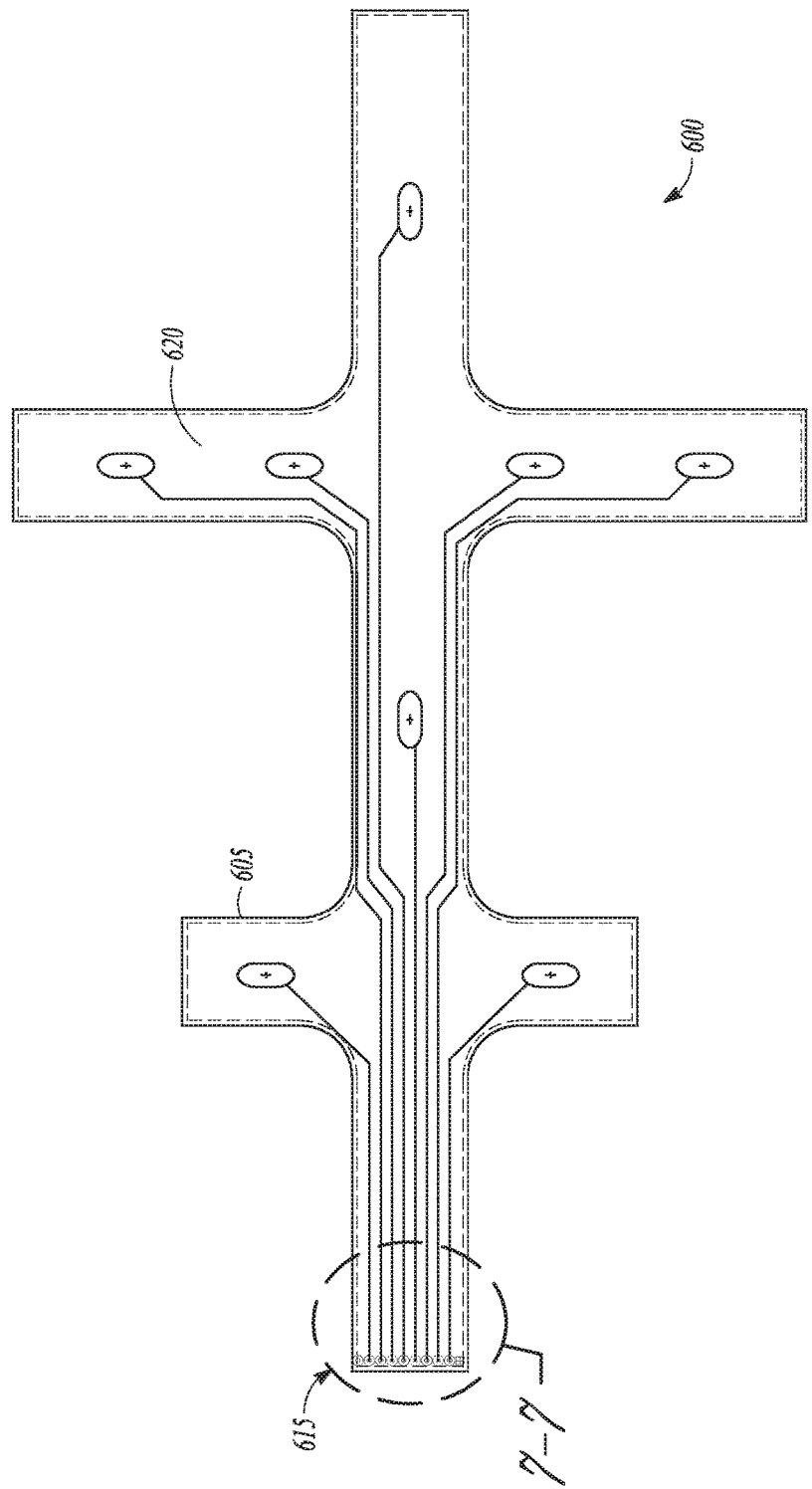

SHIELDED MULTI-CHANNEL EEG HEADSET SYSTEMS AND METHODS

CLAIM OF PRIORITY

This patent application is a U.S. National Stage Filing under 35 U.S.C. 371 from International Patent Application Serial No. PCT/US2013/027464, filed Feb. 22, 2013, published on Aug. 29, 2013 as WO2013/126798A2, which claims the benefit of priority of U.S. Provisional Patent Application No. 61/602,292, entitled "SHIELDED MULTI-CHANNEL EEG CAP SYSTEMS AND METHODS," filed on Feb. 23, 2012, both of which are hereby incorporated by reference herein in their entirety.

BACKGROUND

Typical electroencephalogram (EEG) electrodes are interfaced to EEG recorders discretely through single-conductor connectors. Multi-conductor connectors can be utilized to connect a plurality of electrodes attached to a patient to a recorder. Combined with the recorder's high input impedance (greater than 100 M Ohms, typically), typical electrode-connector arrangements make EEG signals highly susceptible to induced electrical noise.

EEG recorders take advantage of the fact that EEG signals are measured differentially (e.g., recording the difference between a reference and target channel), to improve the signal-to-noise ratio (SNR) of the useful signal by rejecting the common-mode portion. To the extent that induced noise affects both channels, it is rejected.

However, signal path differences between channels, noise distribution, and the relative position of the source of noise, among other factors, contribute to a portion of induced noise affecting each channel independently. These independent differences can be incorrectly treated by a recorder as legitimate EEG signals. EEG recording quality therefore depends on the relative magnitude of the differential EEG and induced noise signals, among other factors, that directly impact the review and patient diagnosis.

OVERVIEW

Induced noise levels can be reduced through shielding electrodes and connectors. Proper shielding of discrete electrodes can be achieved only by applying a shield plane to each channel, for example with a coaxial cable for each electrode. However coaxial cable can be impractical and prohibitive in terms of cost, product complexity and safety concerns.

Traditional electrode caps employ standard EEG electrodes. However, the construction of electrode caps allows electrode conductor bundling, for example in a unified wiring harness, for a portion of the conductor run between the patient and recorder. A unified wiring harness can include a plurality of discrete conductors (e.g., wires) bundled in a ribbon cable and terminated at each end with a connector configured to couple the discrete conductors to corresponding terminals on a recorder. Before reaching the recorder, as well as inside the cap itself, the conductors are separated to allow connectivity and physical electrode positioning.

The use of a wiring harness provides a uniform, or global, shield plane applied to the entire set of channels, by surrounding the harness with a conductive layer connected to a shield potential (typically system ground). Because shield effectiveness depends on the consistent relative position of the shield plane and conductor(s), this approach is not suitable for the unbundled sections of electrode cable. As a result, global shielding is of limited use with traditional electrodes and cap assemblies. In addition, due to safety reasons, no active potentials (such as ground) are available through standard EEG connector interfaces.

An EEG recorder, such as a microEEG™ available from Bio-Signal Group of Brooklyn, N.Y., can utilize a multi-conductor connector to interface with an electrode harness. When an EEG recorder is used with an electrode headset a multi-conductor connector makes EEG recording setup much easier. For example, the electrodes are pre-positioned at specific locations within the electrode headset, which translate into specific physical locations on the patient head when the headset is applied. These locations are associated with specific channel labels that can aid neurologists in correlating the signals collected at each channel with their corresponding electrode location. When using discrete electrodes, the recording technician must be responsible for associating the right channel with a particular physical electrode location on the head of the patient. By using a predefined electrode array and a pre-wired multi-conductor connector, this correlation is therefore assured.

A multi-channel connector also allows the use of a unified wiring harness, and therefore global shielding, over the entire distance between the electrodes and the EEG recorder. In addition, the predefined conductor location allows the supply of an active shield potential without the risk of patient connection. In a traditional cap a portion of the electrode harness would remain unprotected at the individual electrode conductor wiring inside the cap that spread out in order to allow discrete electrode positioning.

A flex circuit-based electrode strip can form a headset that includes the electrode conductors in the plane of the flex circuit, for example, a conductive layer applied on one side of the dielectric maintains a consistent separation distance from the electrodes and conductors on the opposite side of the dielectric. This configuration offers excellent shielding properties that can improve the accuracy of EEG readings. An example flexible headset can include flex circuit strips terminated with a cable connector that provide a shield plane connection that electrically couples the shield plane of the headset and a ground terminal of an EEG recorder electrically through shielding surrounding a cable bundle that contains separate conductors that correspond to each electrode in the headset. Additionally, deployment of an EEG headset as a diagnostic tool in fast-paced and challenging environments such as hospital Emergency Departments can be simplified with a single-use EEG flex-headset by minimizing the time and effort required by a user to properly position and secure the EEG headset.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 6B illustrates an example shield layer of a flex circuit EEG sensor strip, in accordance with some embodiments.

FIG. 6C illustrates an example multi-layer shielded flex circuit EEG sensor strip, in accordance with some embodiments.

DETAILED DESCRIPTION

Figure 1:
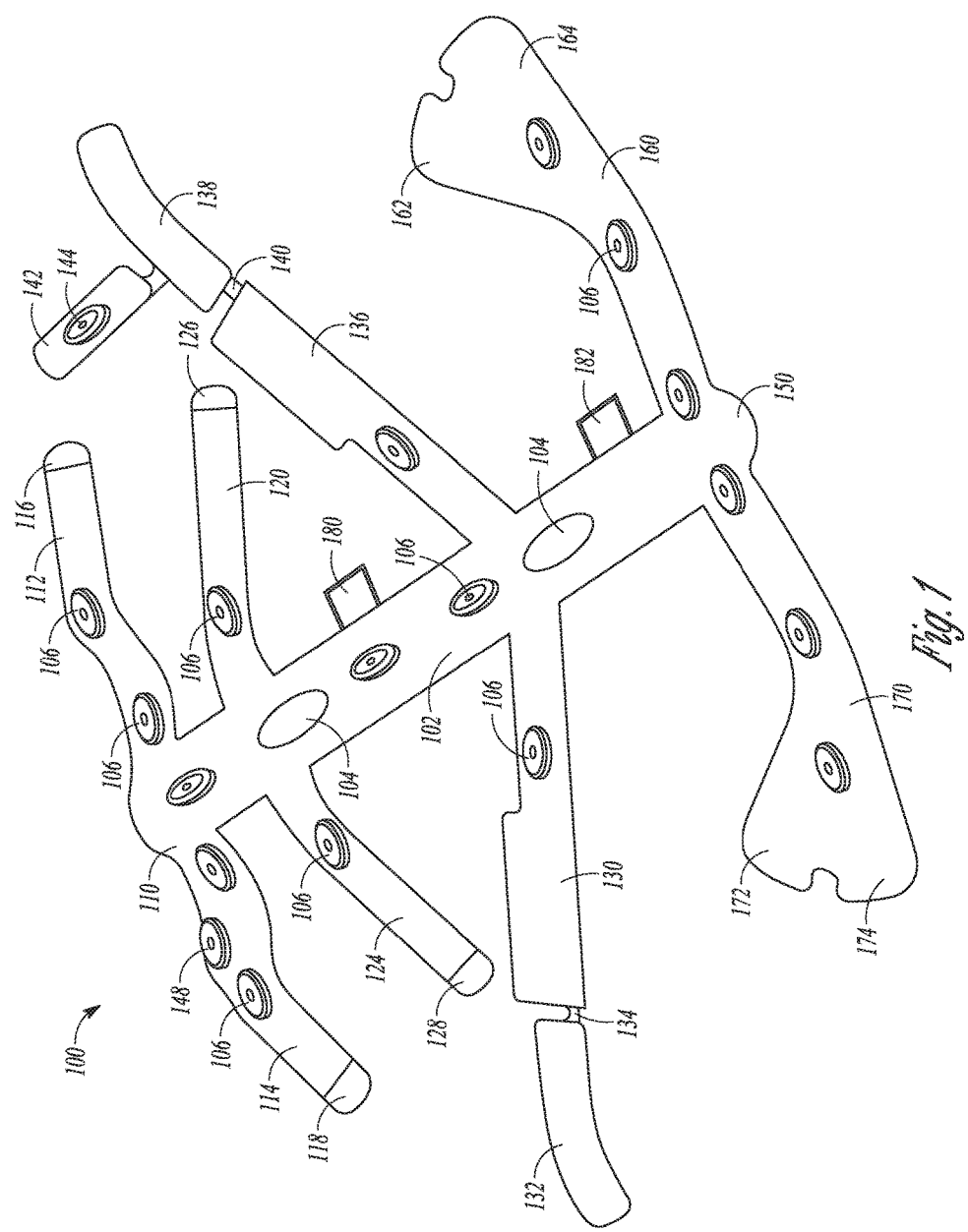
FIG. 1 illustrates an example EEG sensor headset, in accordance with some embodiments.

EEG recorders take advantage of the fact that EEG signals are measured differentially (recording the difference between a reference and target channel), to improve the signal-to noise ratio (SNR) of the useful signal by rejecting the common-mode portion. To the extent that induced noise affects both channels the noise is rejected.

Surface EEG (e.g., non-invasive) electrodes traditionally consist of a small conductive metallic alloy dome welded to a wire for transmitting EEG signals to the recording device. Quality electrical contact with the scalp is achieved by filling the dome cavity with conductive paste or gel, then pressing and securing the electrode to the skin at the desired location. In discrete electrode applications, the surface tension of the conductive paste is enough to keep the electrode in place and ensure contact. In others, a flexible cap material is used to keep electrodes pressed in place. Cap electrodes are generally used in conjunction with electrode gel instead of paste. In order to prevent gel migration during use, cap electrodes are generally mounted in a hollow container filled with gel.

In an example flexible circuit implementation of a sensor headset, the metallic dome can be replaced by an electrode layer of silver-silver chloride that is attached a piece of low-density foam impregnated with conductive gel. A low-tack adhesive layer can surround the electrode area. The sensor headset can be pressed on the head, allowing the foam sponge to compress and make contact with the scalp. The gel can permeate the hair and establish an electrical contact between the scalp and conductive electrode layer.

Additionally, EEG recording interpretations rely on symmetry. For example, brain activity detected by an electrode positioned at a specific location on the left hemisphere is, in a healthy brain, typically expected to show a high degree of symmetry with brain activity detected by an electrode positioned at the corresponding location on the right hemisphere. As a result, a differential measurement performed between electrodes placed at symmetrical locations about a center line, such as an imaginary curve across the top of the head connecting the nasion at the bridge of the nose to the inion where the spinal cord attaches at the back of the head, and at least one reference electrode placed on the center line. With this approach, EEG signals from electrodes that are not on the center line are collected in pairs, from corresponding locations on the left and right sides of the brain. Accurate positioning of pair electrodes, both relative to each other as well as to the center line, can therefore impact the quality of EEG measurements. Electrode positioning standards, such as the International 10-20 System, provide guidance for the specific pair locations to be recorded.

The number of EEG channels used during a recording can vary based on application. For example, a valid EEG can have as few as two channels, such as in an amplitude EEG test performed on a neonate where the electrodes in positions P3 and P4 are monitored. In another example, a valid EEG test can utilize sixteen channels. Other scenarios may utilize other various numbers of EEG sensors as needed. Traditional electrode caps are generally inflexible with regard to the number of electrodes on the cap.

In an example, a sensor headset can provide a twenty sensor configuration, as described by the International 10-20 positioning system, and also a right outer canthus "ROC" channel and a left outer canthus "LOC" channel. In another example, the sensor headset can provide a scaled down implementation of sixteen channels, plus ROC and LOC channels. A flex circuit-based sensor headset implementation can utilize a flat, flexible dielectric layer (insulator) on which conductive traces and electrodes are printed. The conductors for each channel can be distributed anywhere on the surface in a pattern that minimizes the size of the sensor headset, thereby reducing the material and cost required for production of the sensor headset. In an example, a sensor headset can include multi-layer implementations, such as having a dielectric separate two sets of electrode channel conductors or a shield plane. The shield plane can be coupled to an electrical ground.

An advantage of a flex circuit based electrode strip is that the electrode conductors exist only in the plane of the flex circuit, which means that a conductive shield layer applied on the opposite side of the dielectric maintains a consistent separation distance from the electrodes and conductors, and therefore offers excellent shielding properties. An example electrode flex-headset can include flex-circuit strips terminated with a cable connector. A conductive metallic foil 30 included in a shielded ribbon cable can link the flex-headset to an EEG recorder. A middle-layer is conductive metallic foil, and can be connected to the shield potential shield plane of the sensor through exposed terminal conductors.

Combining an EEG electrode harness connector with a flex-circuit headset design can provide a global shield plane to the entire length of conductor, including the electrodes themselves, providing effective induced-noise rejection properties, improved patient comfort, and therefore improved recorded EEG signal quality.

FIG. 1 illustrates an example EEG sensor headset 100, in accordance with some embodiments. In an example, the EEG sensor headset 100 can include an elongated central strip 102 defining one or more electrode-ports 104 and including a plurality of electrodes 106 and a connector 180. The elongated central strip 102 can be sized to cover at least a portion of a center line from a nasal bridge to an occipital protuberance in a posterior part of a patient's head, and being at least partially coated with a first adhesive on a patient side. The first adhesive can maintain a desired electrode contact pressure with the scalp of the patient, while remaining easily removable and minimizing discomfort due to contact with hair.

In an example, the EEG sensor headset 100 can include an anterior member 110 including a first left wing 112 and a first right wing 114. The first left wing 112 and the first right wing 114 can each have at least two electrodes 106. At least a portion of the anterior member 110 can be coated with the first adhesive on the patient side. A left-end portion 116 of the first left wing 112 and a right-end portion 118 of the first right wing 114 can be coated with a second adhesive on the patient side.

In an example, the second adhesive can secure the EEG headset 100 by providing additional support at overlap points, and provide stability at ends points that are positioned over clear skin (e.g., skin that is shaved or otherwise free of hair). The ability to overlap and connect multiple portions of EEG sensor headset can provide physical stability, which can improve the quality of an EEG diagnostic recording.

In an example, the first adhesive can be a low-tack adhesive, and the second adhesive has a higher tack than the first adhesive. The low-tack adhesive can have an adhesive strength such that the EEG sensor headset 100 can be affixed to hair on the patient's head and subsequently removed from the patient without causing pain from the first adhesive pulling the hair during removal. The second adhesive can be affixed to bare skin of the patient, for example on the forehead, cheek, or side of the patient's face where hair is not typically present. In an example, the second adhesive can have a tackiness that is twice as strong as a tackiness of the first adhesive. In an example, the second adhesive can include an application of the first adhesive at an application rate that is twice the thickness of an application rate of first adhesive, resulting in the second adhesive being formulaically identical to the first adhesive, but having a tackiness that is twice as strong as the tackiness of the first adhesive. In an example, an adhesive can include an acrylate and dispersion based pressure-sensitive adhesive that does not cause skin irritation, such as KIWOPRINT® TATTOO D 164, available from Kissel & Wofi GmbH of Mannheim, Germany or KIWO, Inc. of Seabrook, Tex., which can be utilized as the first adhesive when applied with a first thickness, and the second adhesive when applied with a second thickness that is greater than the first thickness.

In an example, the EEG sensor headset 100 can include a second anterior member including a second left wing 120 and a second right wing 124. The second left wing 120 and the second right wing 124 can each have an electrode 106. At least a portion of the second anterior member can be coated with the first adhesive on the patient side. A left-end portion 126 of the second left wing 120 and a right-end portion 128 of the second right wing 124 can be coated with the second adhesive on the patient side.

In an example, the EEG sensor headset 100 can include a right side member 130 including an electrode 106, at least a portion of the right side 130 member being coated with the first adhesive, and a right contact member 132 coupled to the right side member 130 by a first lateral flex joint 134. The right contact member 132 can be coated with the second adhesive on the patient side.

Lateral flex joints (LFJ) can be formed in a flex circuit by removing a portion of the flex circuit strip, thereby providing a bendable joint perpendicular to a plane of the flex strip while maintaining rigidity within the plane. LFJ can include cutout areas, cleared of adhesive layers, which facilitate localized outward bowing of the flex circuit material and thereby allow side-to-side adjustments of adjacent strip components. This provides flexibility in an EEG sensor headset that allows the EEG sensor headset to take on a shape that conforms to a variety of head sizes. LFJ can include one or more traces that can couple an electrode 106 with the connector 180.

In an example, the EEG sensor headset 100 can include a left side member 136 including an electrode 106, a portion of the left side member being coated with the first adhesive on the patient side, and a left contact member 138 coupled to the left side member 136 by a second lateral flex joint 140. The left contact member 138 can be coated with the second adhesive on the patient side. In an example, the EEG sensor headset 100 can include a posterior member 150 coated with the first adhesive. The posterior member 150 can include a third left wing 160 having at least three electrodes 106 on the patient side, and an upper external adhesion location 162 and a lower external adhesion location 164 coated with the second adhesive on an outer side opposite the patient side. The posterior member 150 can include a third right wing 170 having at least three electrodes 106 on the patient side, and an upper external adhesion location 172 and a lower external adhesion location 174 coated with the second adhesive on the outer side.

In an example, the EEG sensor headset 100 can include a connector 180 disposed on the elongated central strip 102 between the anterior member 110 and the posterior member 150. The connector 180 can electrically couple to the electrodes 106 by respective traces. The connector 180 can include a terminal corresponding to the respective electrodes 106.

In an example, the EEG sensor headset 100 can include a shield plane coupled to a flexible outer substrate. The flexible outer substrate can provide a backing to the EEG sensor headset 100. A dielectric material can be disposed between the shield plane and the electrodes 106, such that the shield plane is opposite the patient side of the electrodes and the electrodes are disposed on the dielectric material.

In an example, the EEG sensor headset 100 can include a second connector 182 electrically-coupled to some of the electrodes 106 by a plurality of traces, the second connector 182 including a terminal corresponding to each respective electrode. The connector 180 can be coupled to the electrodes 106 that are not electrically connected to the second connector 182. In an example, the connector 180 and the second connector 182 can both include a shield terminal that is electrically coupled to the shield plane.

In an example, the EEG sensor headset 100 can include a third electrode 148 disposed on the first right wing 114 of the anterior member 110, and a lower ocular member 142 having an electrode 144, coupled to the left contact member 138 by a third lateral flex joint 146. The second lateral flex joint 140 and the third lateral flex joint 146 can include a trace electrically coupling the electrode 144 of the lower ocular member 142 to the connector 180. In an example, the first lateral flex joint 134, the second lateral flex joint 140, and the third lateral flex joint 146 can have a width that is less than one-half a width of the elongated central strip 102.

In an example, the EEG sensor headset 100 can include at least nineteen electrodes that provide at least sixteen EEG channels and one or more reference channels. The EEG sensor headset 100 can include an electrode providing a LOC channel, and an electrode providing a ROC channel. In an example, the EEG sensor headset 100 can include a plurality of dual-layer foam reservoirs, each one of the plurality of dual-layer foam reservoirs coupled to an electrode. An inner layer of the plurality of dual-layer foam reservoirs can include a conductive gel. In an example, the EEG sensor headset 100 can include a plurality of partial perforations in the flexible outer substrate, each partial perforation corresponding to a location of one of the electrodes.

In an example, the EEG sensor headset 100 can be affixed to the head of patients with various sizes of heads such that the elongated central strip 102 covers the center line of the patient (e.g., from nasion to inion) such that the left-end portion 116 of the first left wing 112 is releasably adhered to the lower external adhesion location 164 of the third left wing 160, the left-end portion 126 of the second left wing 120 is releasably adhered to the upper external adhesion location 162 of the third left wing 160, and the left side member 136 is releasably adhered to the left-end portion 116 of the first left wing 112 and the third left wing 160. In a similar manner, the right-end portion 118 of the first right wing 114 is releasably adhered to the lower external adhesion location 174 of the third right wing 170, the right-end portion 128 of the second right wing 124 is releasably adhered to the upper external adhesion location 172 of the third right wing 170, and the right side member 130 is releasably adhered to the right-end portion 118 of the first right wing 114 and the third right wing 170.

Figure 2:
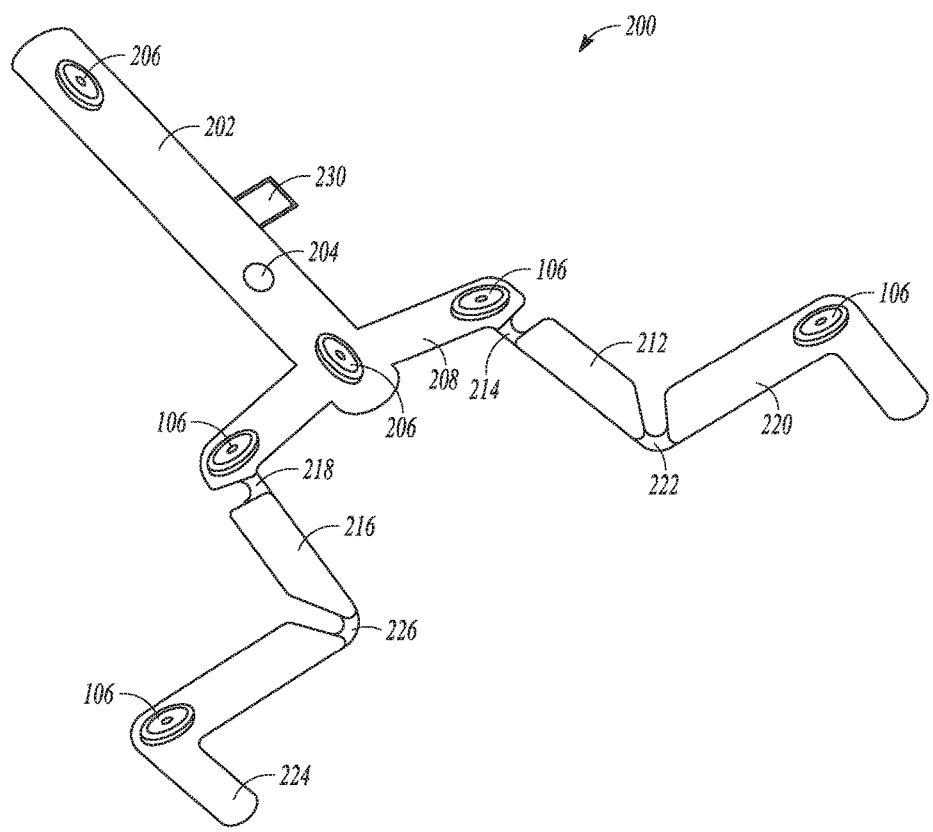
FIG. 2 illustrates an example auxiliary sensor headset assembly, in accordance with some embodiments.

FIG. 2 illustrates an example auxiliary sensor headset assembly 200, in accordance with some embodiments. The auxiliary sensor assembly 200 can include a center strip 202, an electrode access location 204, and a pair of electrodes 206 configured to mate with the pair of electrode ports 104 of the elongated central strip 102 of the EEG sensor headset 100 of FIG. 1. The mating of the pair of electrodes 206 with the pair of electrode port 104 can provide a secure, repeatable, and predictable physical connection between the auxiliary sensor assembly 200 and the EEG sensor headset 100. The electrode access location 204 can provide physical access to an electrode 106 disposed on the elongated central strip 102 of the EEG sensor headset 100.

In an example, the auxiliary sensor assembly 200 can include a left auxiliary wing 208 having an electrode 106 and a right auxiliary wing 210 having an electrode 106. The left auxiliary wing 208 can be coupled to a left extension 212 by a fourth lateral flex joint 214. The right auxiliary wing 210 can be by coupled to a right extension 216 by a fifth lateral flex joint 218. A left ear piece 220, having an electrode 106, can be coupled to the left extension 212 by a sixth lateral flex joint 222. A right ear piece 224, having an electrode 106, can be coupled to the right extension 216 by a sixth lateral flex joint 226. In an example, the auxiliary sensor assembly 200 can include a connector electrically coupled to each of the electrodes 106 and the pair of electrodes 206 by a respective trace.

In an example, the auxiliary sensor assembly 200 can include a shield plane coupled to a flexible outer substrate. The flexible outer substrate can provide a backing to the auxiliary sensor assembly 200. The flexible outer substrate can provide a dielectric material disposed between the shield plane and the electrodes 106 and the pair of electrodes 206, such that the shield plane is opposite the patient side of the electrodes and the electrodes are disposed on the dielectric material.

Figure 3A:
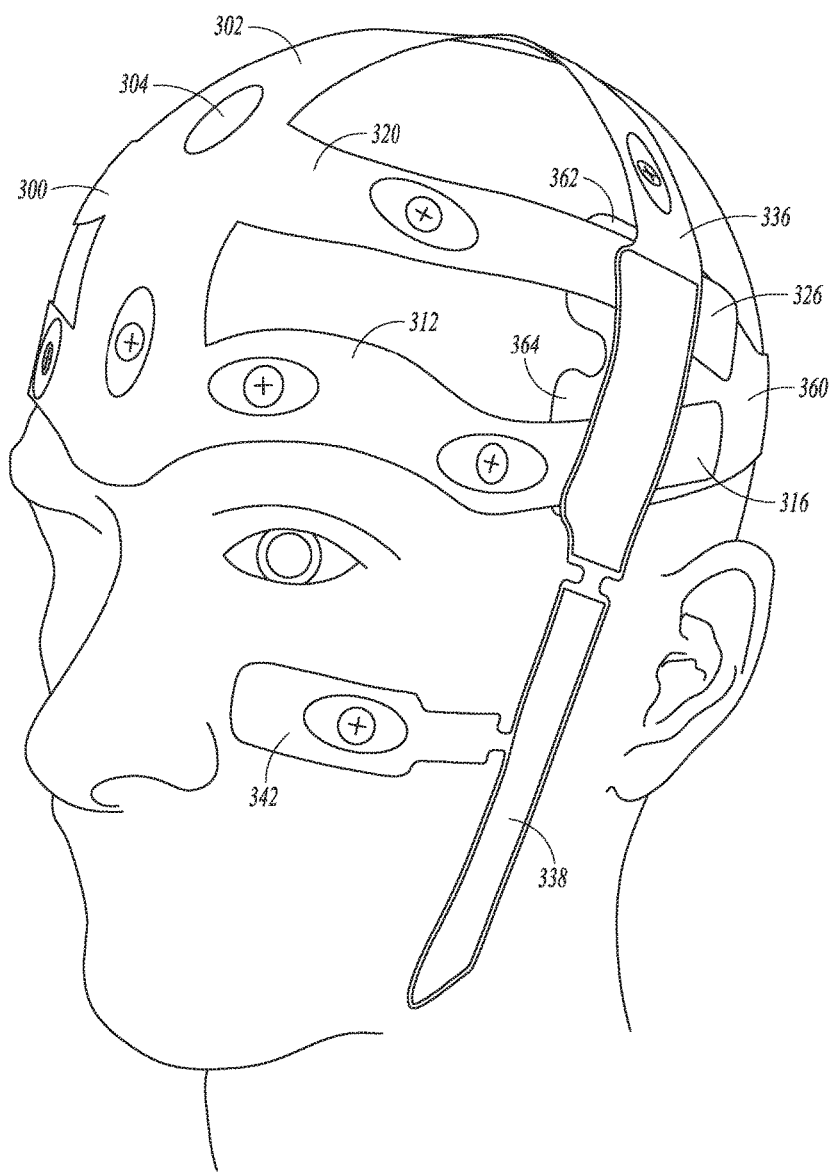
FIG. 3A-3C illustrate an example EEG sensor headset, in accordance with some embodiments.

FIG. 3A illustrates an example EEG sensor headset 300, in accordance with some embodiments. The EEG sensor headset 300 can include an embodiment of EEG sensor headset 100 of FIG. 1.

For example, the EEG sensor headset 300 includes an elongated central strip 302 with opening 304 (e.g., electrode-port 104) disposed over the center line of the patient such that a left-end portion 316 of a first left wing 312 is releasably adhered to a lower external adhesion location 364 of a third left wing 360, a left-end portion 326 of a second left wing 320 is releasably adhered to an upper external adhesion location 362 of a third left wing 360, and a left side member 336 is releasably adhered to the left-end portion 316 of the first left wing 312 and the third left wing 360. A left contact member 338 can be coupled by a lateral flex joint to the left side member 336. A lower ocular member 342 can be coupled to a left contact member 338 by a lateral flex joint.

Figure 3B:
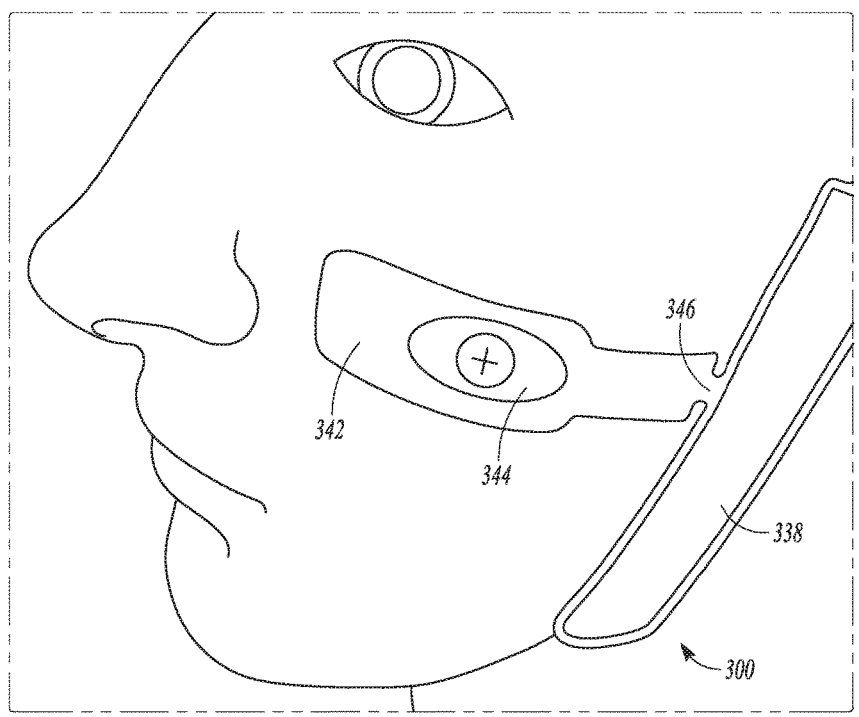

FIG. 3B illustrates an example EEG sensor headset 300, in accordance with some embodiments. As shown generally in FIG. 3A, the EEG sensor headset 300 can include a LOC electrode 344 on the lower ocular member 342 disposed below a patient's left eye. The lower ocular member 342 can be coupled to the left contact member 338 of the EEG sensor headset 300 by a lateral flex joint 346. The lateral flex joint 346 can allow the lower ocular member 342 to be adjusted up or down relative to the EEG sensor headset 300 such that the lower ocular member 342 is properly positioned below the patient's left eye. The lower ocular member 342 can include an adhesive opposite the electrode such that the lower ocular member 342 can be folded back and adhered to the left contact member 338. The lateral flex joint 346 can be bent at an angle of approximately 180 degrees, thereby completely folding the lower ocular member 342 away from the patient's left eye.

Figure 3C:
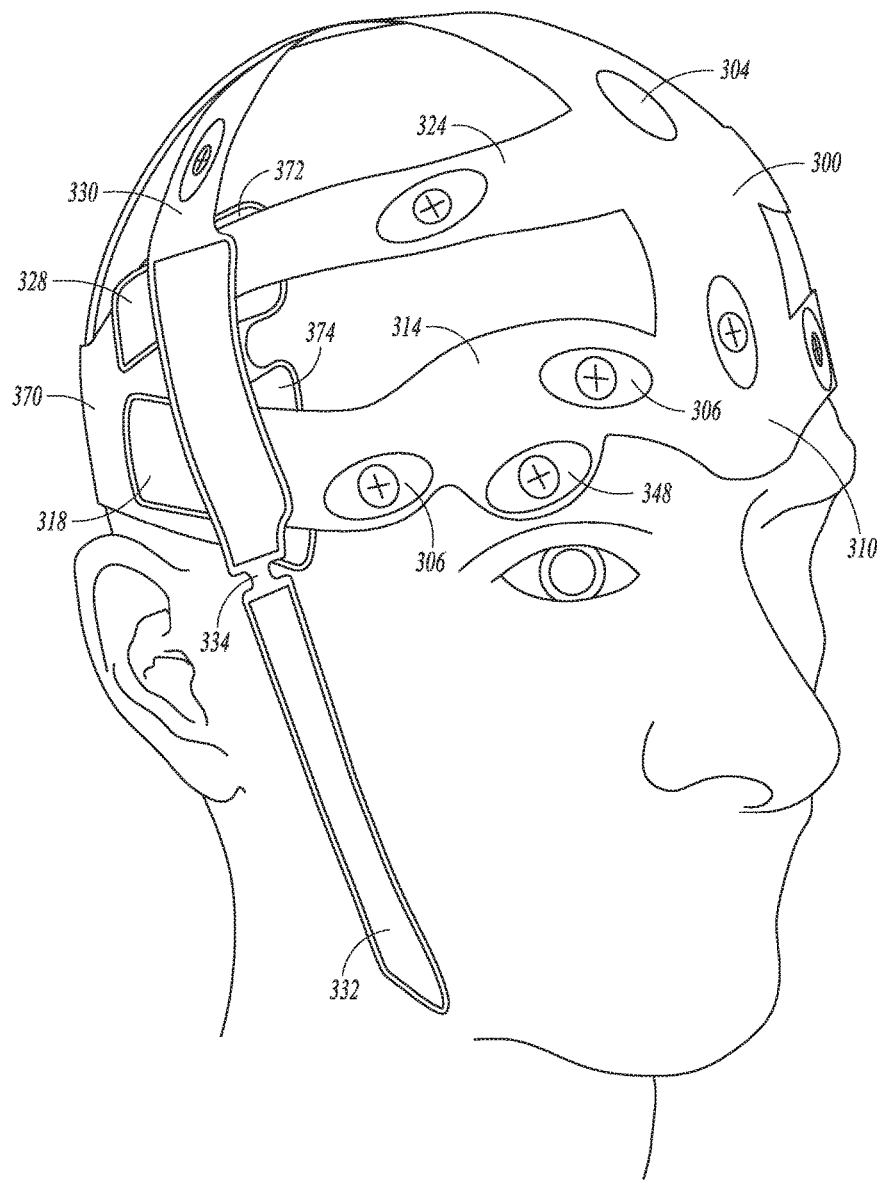

FIG. 3C illustrates an example EEG sensor headset 300, in accordance with some embodiments. In an example, the EEG sensor headset 300 can include an anterior member 310 with a first right wing 314. The first right wing 314 can each have at least two electrodes 306. A right-end portion 318 of the first right wing 314 can be coated with an adhesive. The EEG sensor headset 300 can include a second right wing 324 having a right-end portion 328. The EEG sensor headset 300 can include a right side member 330 including an electrode 106, at least a portion of the right side 330 member being coated with the first adhesive, and a right contact member 332 coupled to the right side member 330 by a first lateral flex joint 334. The posterior member of EEG sensor headset 300 can include a third right wing 370 having an upper external adhesion location 372 and a lower external adhesion location 374.

As illustrated in FIG. 3C, the right-end portion 318 of the first right wing 314 can be releasably adhered to the lower external adhesion location 374 of the third right wing 370, the right-end portion 328 of the second right wing 324 can be releasably adhered to the upper external adhesion location 372 of the third right wing 370, the right side member 330 can be releasably adhered to the right-end portion 318 of the first right wing 314, the right-end portion 328 of the second right wing 324, and the third right wing 370.

Figure 4A:
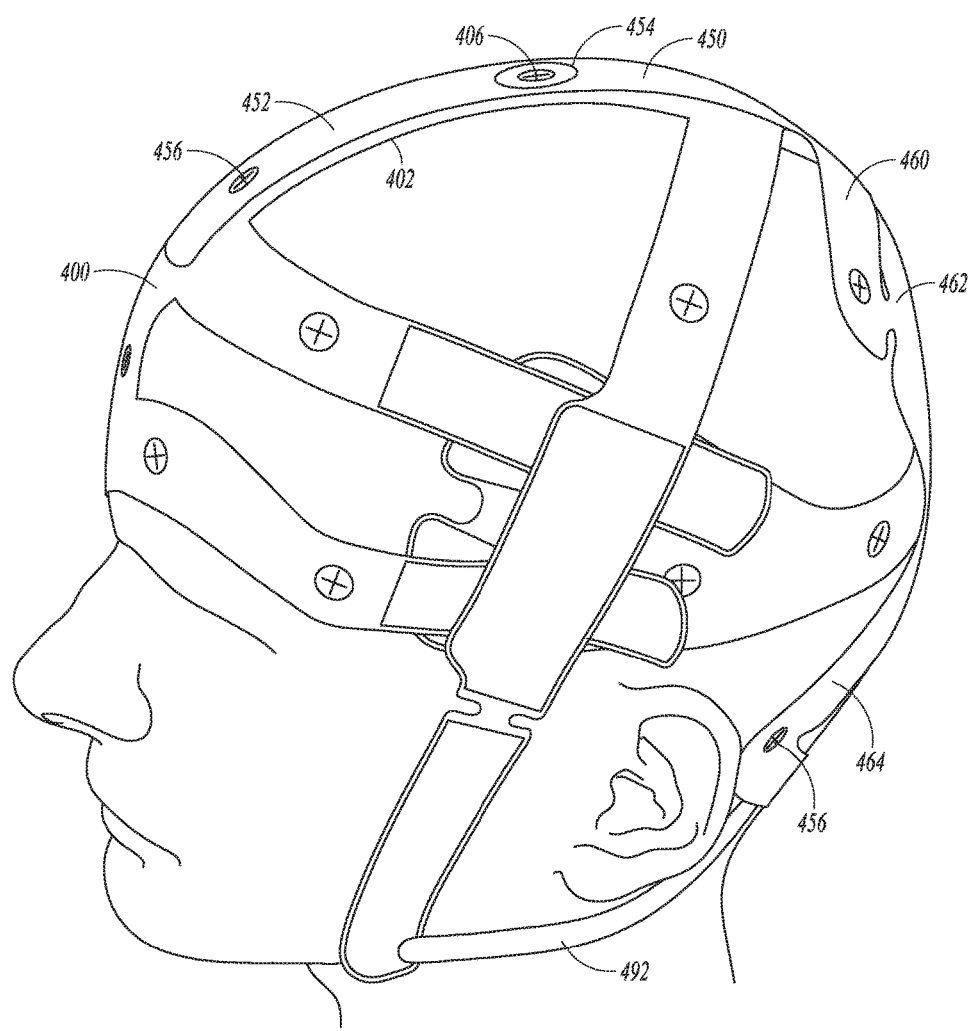
FIG. 4A illustrates a side view of an example EEG sensor headset and auxiliary sensor, in accordance with some embodiments.

FIG. 4A illustrates a side view of an example EEG sensor headset 400 and an auxiliary sensor 450, in accordance with some embodiments. In an example, the EEG sensor headset 400 does not include the lower ocular member 342 or right ocular member 348 of EEG sensor headset 300. The EEG sensor headset 300 can otherwise include the members, wings, and electrodes as presented in FIGS. 3A-3C above. In an example, the auxiliary sensor 450 can be coupled to the EEG sensor headset 400 after the EEG sensor headset 400 is affixed to a patient's head, or prior to being the combination of the EEG sensor headset 400 and the auxiliary sensor 450 being placed on the patient.

In an example, the auxiliary sensor assembly 450 can include a central member 452 defining a port 454 and having one or more electrodes 456 configured to mate with an electrode port(s) of the elongated central strip. The port 404 can be disposed at a location along the central member 404 such that an electrode 406 of the elongated central strip 402 is accessible through the opening defined by port 454.

Figure 4B:
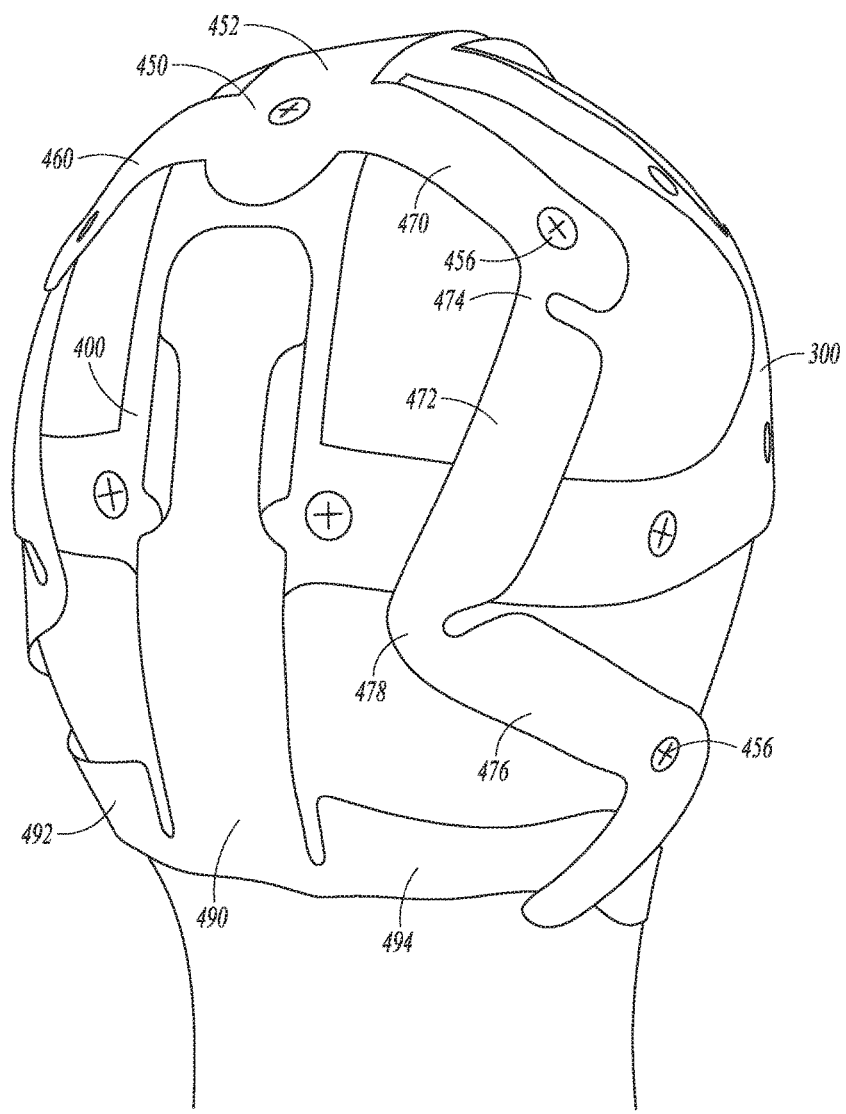
FIG. 4B illustrates a rear view the example EEG sensor headset and auxiliary sensor of FIG. 4A, in accordance with some embodiments.

In an example, the auxiliary sensor assembly 450 can include a left auxiliary wing 460 having an electrode 456. A left extension 462 can be coupled to the left auxiliary wing by a lateral flex joint. A left ear piece 464, having an electrode 456, can be coupled to the left extension 462 by a lateral flex joint. FIG. 4B illustrates a rear view the example EEG sensor headset and auxiliary sensor of FIG. 4A, in accordance with some embodiments. In an example, the auxiliary sensor assembly 450 can include a right auxiliary wing 470, having an electrode 456, and a right extension 472 coupled to the right auxiliary wing 470 by a fifth lateral flex joint 474. A right ear piece 478, having an electrode 456, can be coupled to the right extension 472 by a lateral flex joint 478.

In an example, one or more tie down strips 490 that can be attached to the EEG sensor headset 400. The one or more tie down strips 490 may include a left-side strip 492 and a right-side strip 494. Tie down strips 490 may include flat flexible substrate material and one or more adhesives. Tie down strips 490 generally do not include traces, connectors or electrodes. Tie down strips 490 can have various sizes and be utilized to secure EEG sensor headset 400 to a patient's head. For example, in a scenario where a patient has long or dense hair a tie-down strip 490 may be utilized to provide extra support to secure the EEG sensor headset 400 to the patient.

Figure 4C:
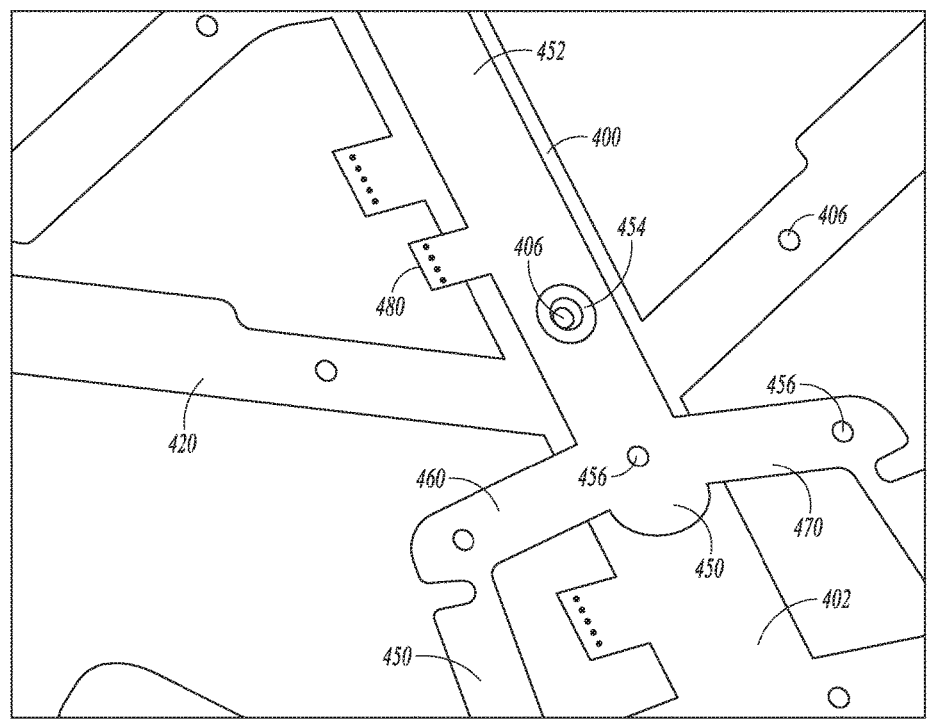
FIG. 4C illustrates a partial view of an example EEG sensor headset and auxiliary sensor headset assembly, in accordance with some embodiments.

FIG. 4C illustrates a partial view of an example EEG sensor headset 400 and auxiliary sensor headset assembly 450, in accordance with some embodiments. In an example, the auxiliary sensor assembly 450 can include a connector 480 electrically coupled to the electrodes by a plurality of traces, each trace connecting a single electrode to an individual terminal of the connector. In an example, as depicted in FIG. 4C, the central member 452 can define the port 454 such that an electrode 406 of the elongated central strip 402 is accessible through the opening defined by port 454.

Figure 5:
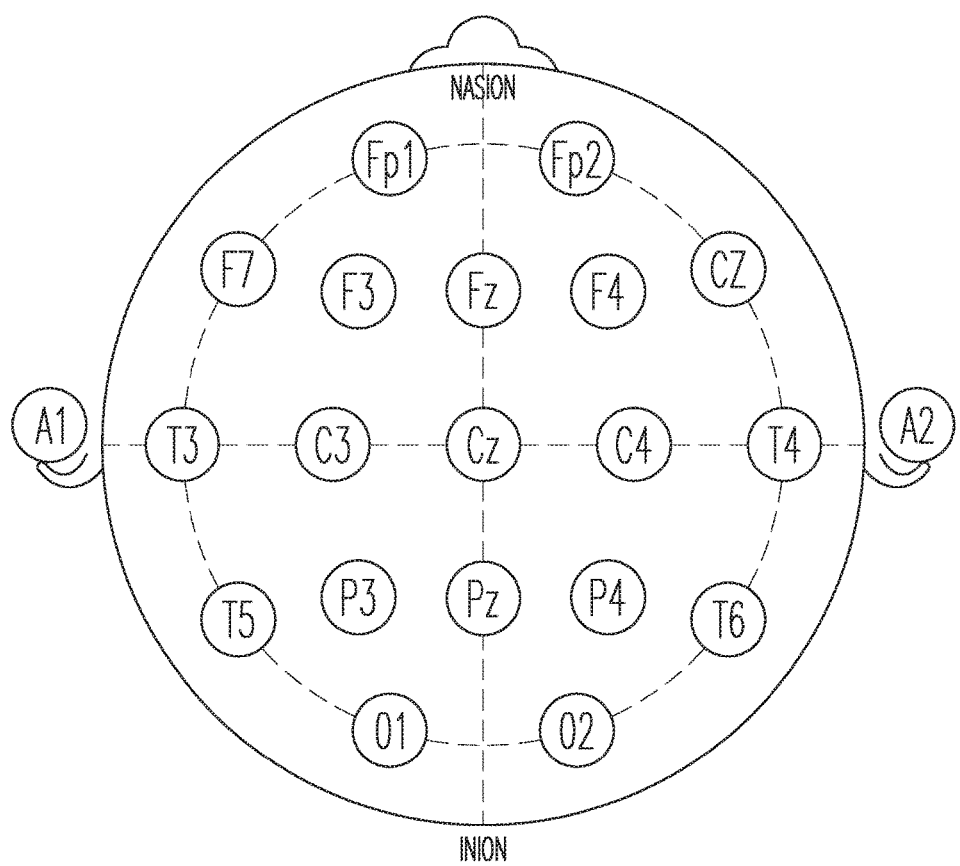
FIG. 5 illustrates an example electrode sensor layout of the prior art.

FIG. 5 illustrates an example electrode sensor layout of the prior art that can conform to the guidelines provided in the International Standard 10-20 System.

In an example, the electrode sensor layout of the International Standard 10-20 System can be provided by an example embodiment of the EEG sensor headset 400 and auxiliary sensor headset assembly 450 having, in combination, at least twenty-one electrodes arranged according to the International Standard 10-20 System.

Figure 6A:
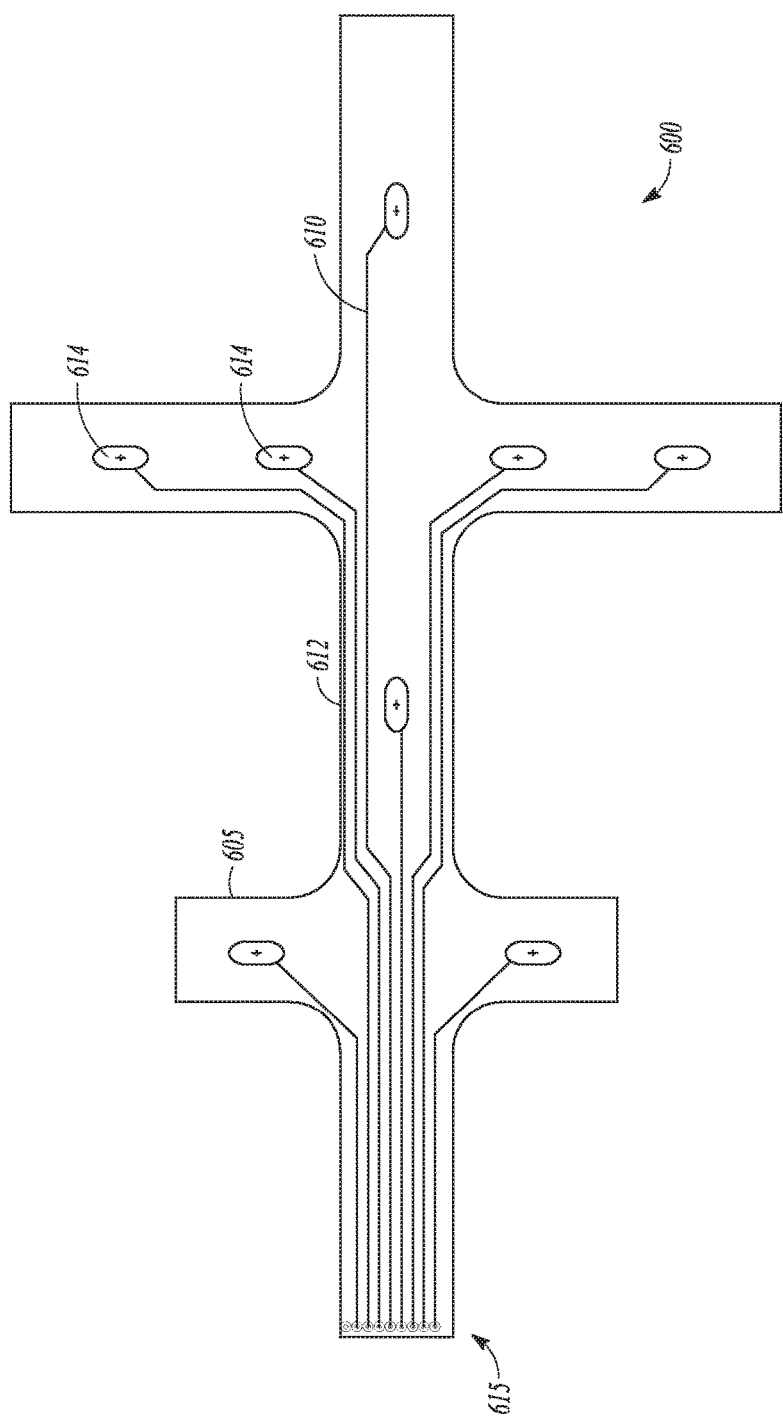
FIG. 6A illustrates an example flex circuit EEG sensor strip, in accordance with some embodiments.

FIGS. 6A-6C illustrate various layers of an example embodiment of a shielded flex circuit EEG sensor strip.

FIG. 6A illustrates an example shielded flex circuit EEG sensor strip 600, in accordance with some embodiments. In an example, the EEG sensor strip 600 is outlined in the shape of an EEG sensor headset by a dielectric material 605 forming a flexible substrate. An electrode layer 610 is included on one side (e.g., a patient facing side) of the dielectric material 605. The electrode layer 610 can include both conductive traces 612 and electrode sensors 614. The electrode layer 610 can include a cable attachment portion 615 (e.g., a connector) that consolidates the conductive traces 612 from the electrodes 614 at a suitable location for coupling the electrodes, via the traces, to an EEG recorder.

FIG. 6B illustrates an example shield layer 620 of a flex circuit EEG sensor strip 600, in accordance with some embodiments. In an example, the shield plane layer 620 is disposed on a side of the dielectric material 605 that is opposite the electrode layer 610 of FIG. 6A. The shield plane layer 620

FIG. 6C depicts an example embodiment of a shielded flex circuit EEG sensor strip 600 that includes an electrode layer 610, a dielectric material 605, and a shield plane layer 620 that are stacked together to form an exemplary grounded flexible multi-electrode EEG sensor assembly.

Figure 7:
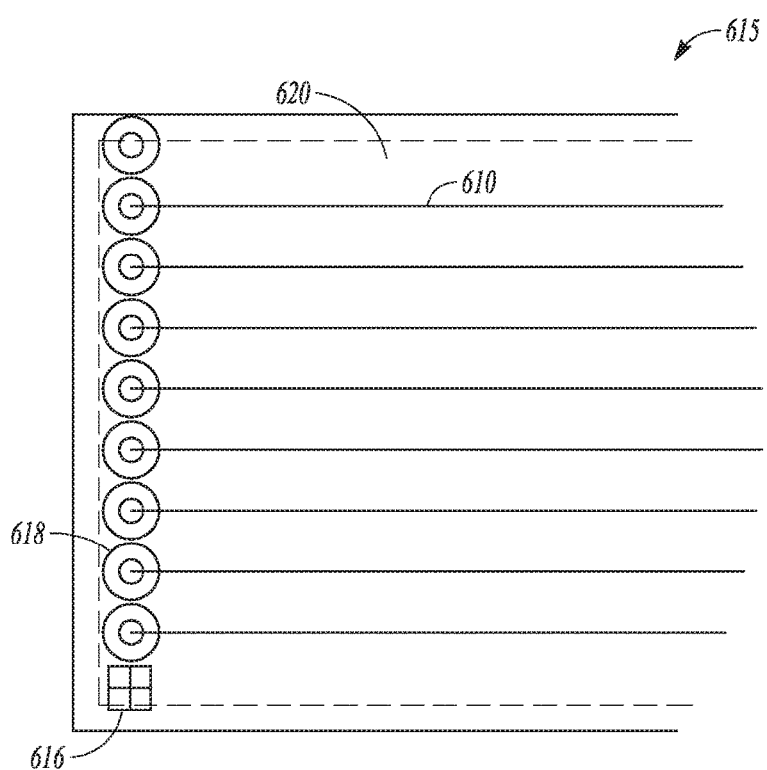
FIG. 7 illustrates a detail view of an example connector of a multi-layer shielded flex circuit EEG sensor strip, in accordance with some embodiments.

FIG. 7 illustrates a detail view of an example connector 615 of a multi-layer shielded flex circuit EEG sensor strip 600, in accordance with some embodiments. In an example, connector 615 can include one or more shield-plane connections 616 and electrode terminals 618. The one or more shield-plane connections 616 and electrode terminals 618 can be coupled to an electrode harness cable interface and thereby electrically connected to an EEG recorder. Shielding can be therefore continuously provided from the individual electrodes to the EEG recorder by the shield plane layer 620 and a shielded multi-conductor cable.

Figure 8:
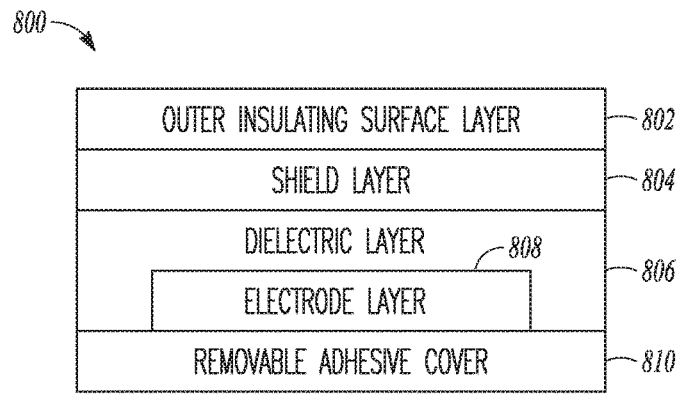
FIG. 8 illustrates a cross-sectional view of an example EEG sensor assembly, in accordance with some embodiments.

FIG. 8 illustrates a cross-sectional view of an example EEG sensor assembly 800, in accordance with some embodiments. In an example, the EEG sensor assembly 800 includes an outer insulating surface 802, a shield layer 804 that can be coupled to a ground terminal of an EEG recorder, a dielectric layer 806 that can form a flexible substrate that the shield layer 804 is printed on, an electrode layer 808 that can be printed or etched onto the dielectric layer 806, and a removable adhesive cover 810 that can protect the electrode layer 808 until the EEG assembly is ready for use.

In an example, EEG sensor assembly 800 can also include a memory shape film or foil that can bias the EEG sensor assembly 800 into a concave shape that can conform to the shape of the head of a patient. The memory shape film or foil can be included as a separate layer or integrated as part of another layer.

In an example, the dielectric layer 806 can have a thickness of approximately two mil. The grounded shield layer 804 can be a copper or copper-alloy material or film. The dielectric layer 806 can be a polyester or polyimide material or film. The electrode layer 808 can be a silver or silver-chloride material or film. Additional embodiments with similar or equivalent materials are also contemplated.

Figure 9:
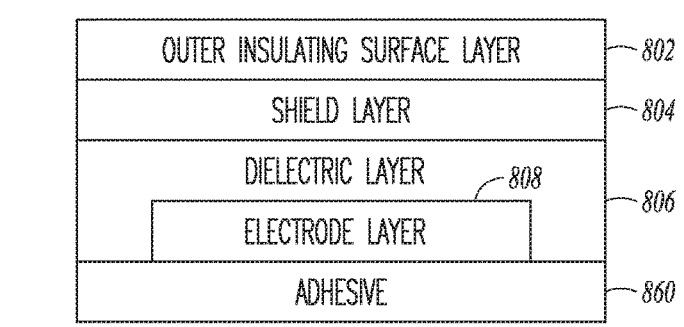
FIG. 9 illustrates a cross-sectional view of an example EEG sensor assembly, in accordance with some embodiments.

FIG. 9 illustrates a cross-sectional view of an example EEG sensor assembly 850 that includes an outer insulating surface layer 802, a grounded shield layer 804, a dielectric layer, an electrode layer 808, and an adhesive layer 860 that can removably attach the EEG sensor assembly 850 to a patient.

Figure 10:
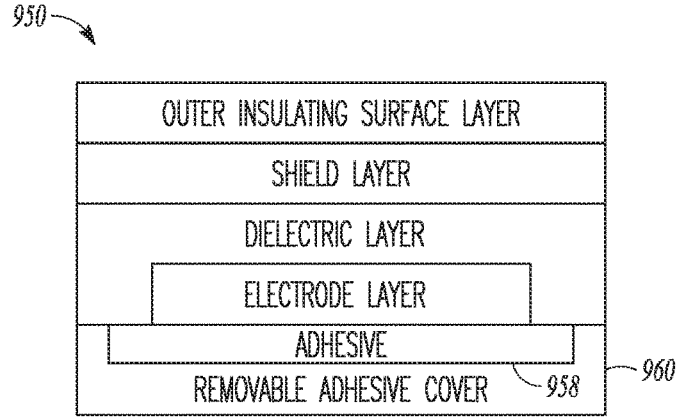
FIG. 10 illustrates a cross-sectional view of an example EEG sensor assembly, in accordance with some embodiments.

FIG. 10 illustrates a cross-sectional view of an example EEG sensor assembly 950, in accordance with some embodiments. The example EEG sensor assembly 950 can include a removable cover 960 to protect the electrode layer and surrounding adhesive layer 958 prior to use. The removable cover 960 can be peeled off of the EEG sensor assembly 950 while the adhesive 958 remains in contact with the EEG sensor assembly 950.

Figure 11:
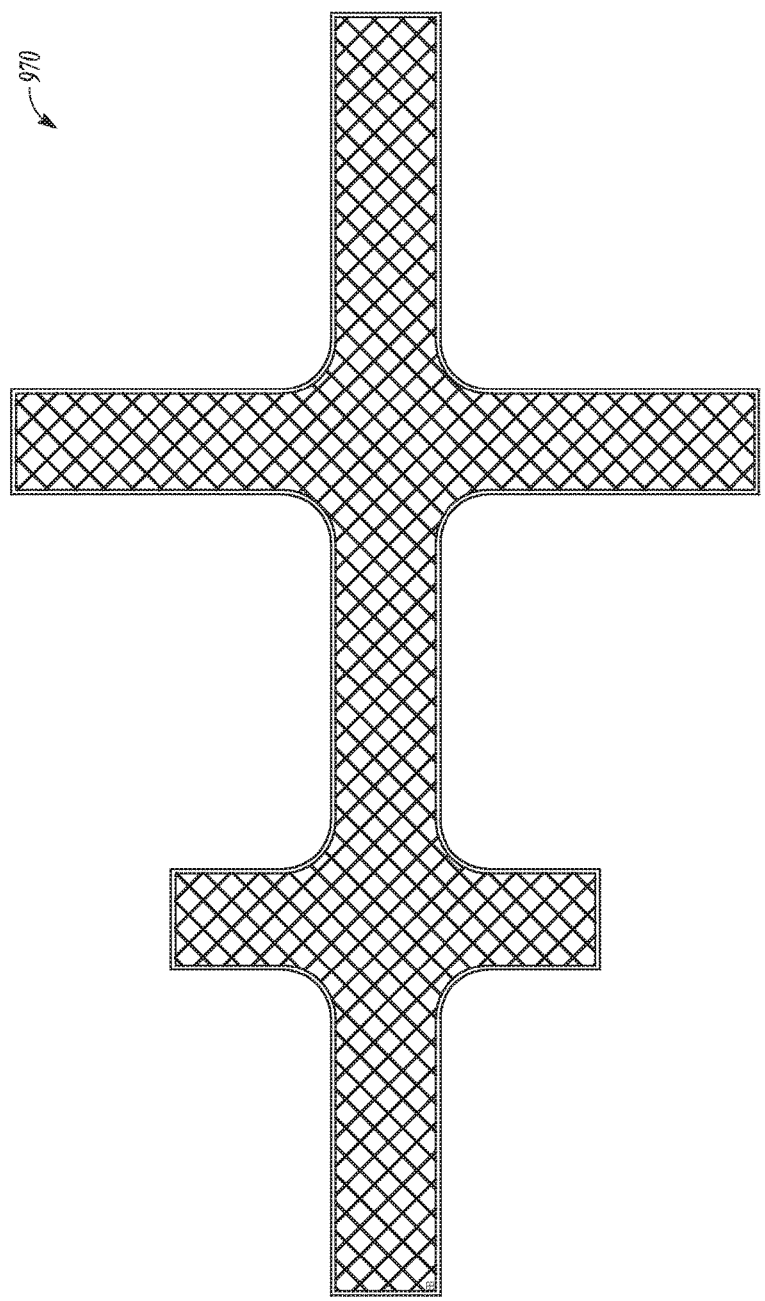
FIG. 11 illustrates an example cross-hatched shield layer of a flex circuit EEG sensor strip, in accordance with some embodiments.

FIG. 11 illustrates an example cross-hatched shield layer of a flex circuit EEG sensor assembly, in accordance with some embodiments. In an example, shield plane 970 can include a conductive layer that is printed on the dielectric in a cross-hatch or lattice pattern. Alternative patterns such as a grid or array configuration are also contemplated. The traces or openings in a grid or lattice pattern can be sized such that interference from ambient electromagnetic noise is reduced or eliminated, while providing the EEG sensor assembly with the capability of flexing to easily conform to the shape of a patient's head. The shield plane 970 with a cross-hatch or another perforated design can be utilized with any one of the EEG sensor assemblies or strips discussed herein.

Figure 12:
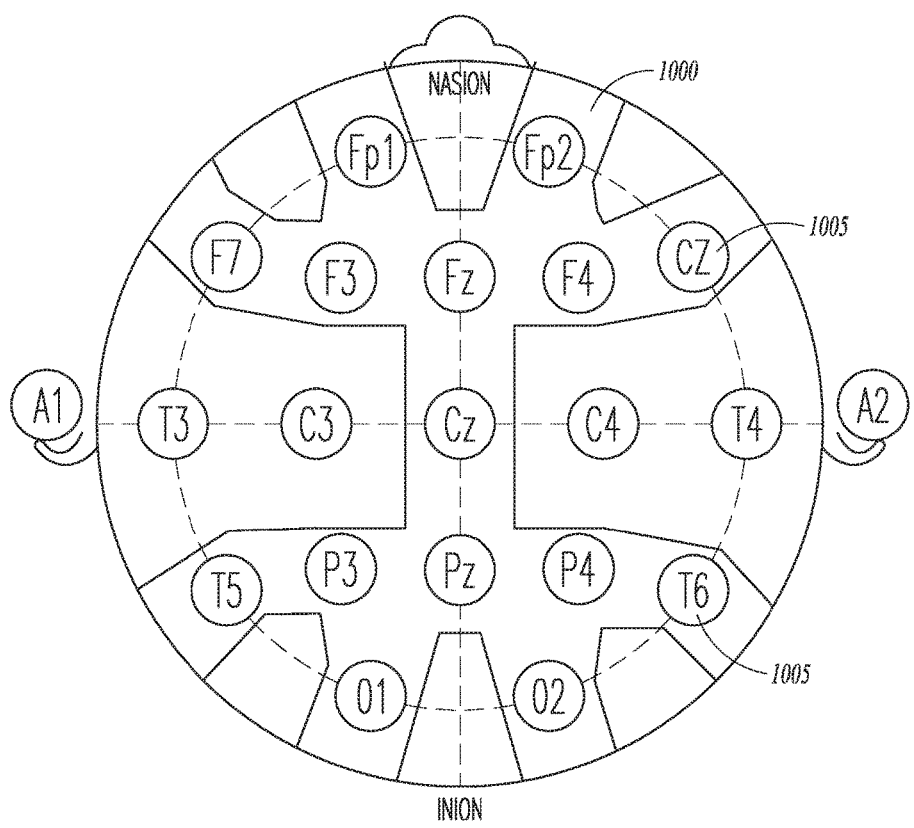
FIG. 12 illustrates an example of an EEG sensor assembly, in accordance with some embodiments.

FIG. 12 illustrates an example of an EEG sensor assembly 1000 that includes a plurality of electrodes 1005 that can be distributed throughout the EEG sensor assembly 1000. The electrodes 1005 can be printed on a first side of a dielectric strip that provides the outline of the EEG sensor assembly 1000. A shield plane, such as those depicted in FIG. 6B or FIG. 11, can be printed on a second side of the dielectric strip opposite the first side.

Figure 13:
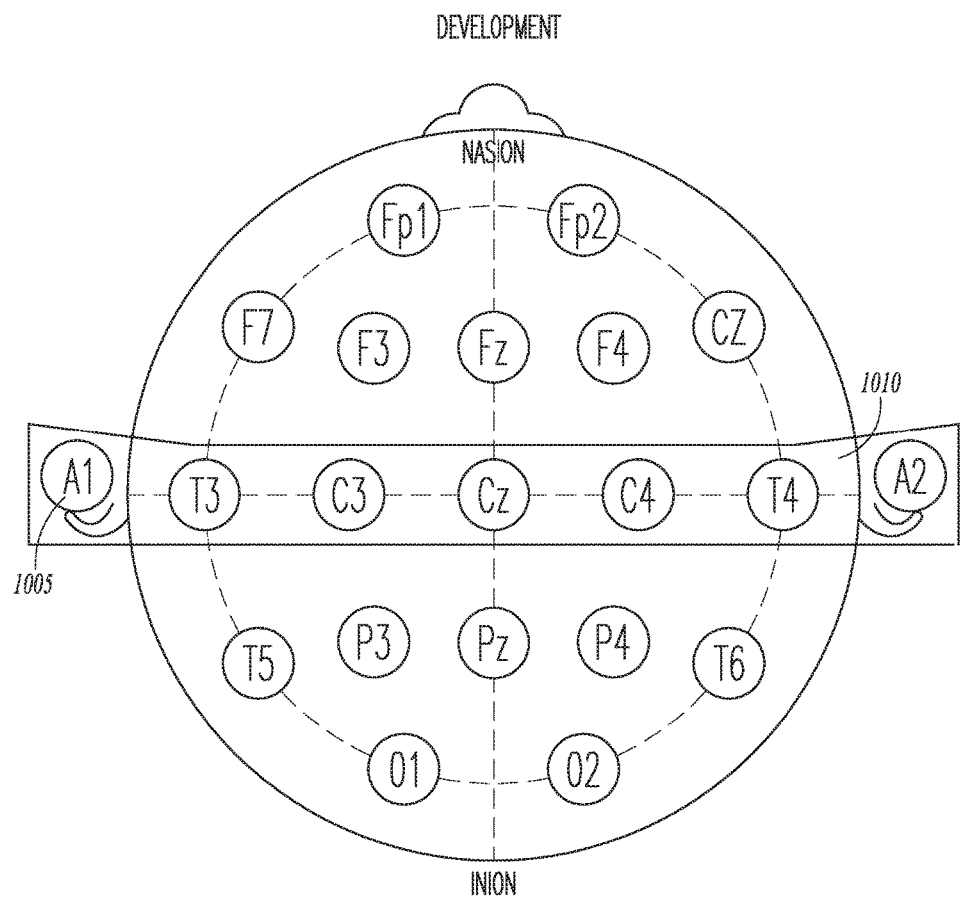
FIG. 13 illustrates an example of a separate EEG sensor assembly strip, in accordance with some embodiments.

FIG. 13 illustrates an example of a separate EEG sensor assembly strip 1010 that can be used alone, or in combination with EEG sensor assembly 1000 to provide coverage of all of the electrode placement locations as suggested by a standard 10-20 electrode pattern. Each individual EEG sensor assembly can include its own connector to individual traces in the assembly, thereby coupling each electrode to an EEG reader.

Figure 14:
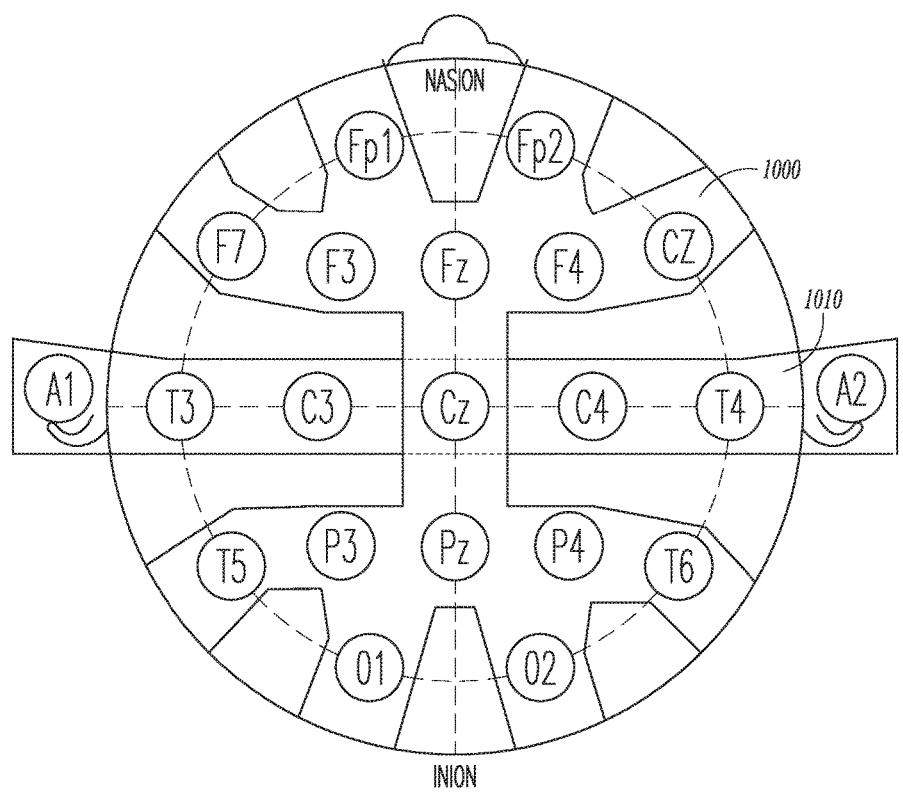
FIG. 14 illustrates an example of an EEG sensor assembly and an EEG sensor assembly strip, in accordance with some embodiments.

FIG. 14 illustrates an example of both the EEG sensor assembly 1000 and the EEG sensor assembly strip 1010 disposed over the top of the head of a patient. In an example embodiment the electrodes are spaced apart in the EEG sensor assembly 1000 such that the electrodes conform to some or all of the electrode placement locations as suggested by a standard 10-20 electrode pattern.

Figure 15:
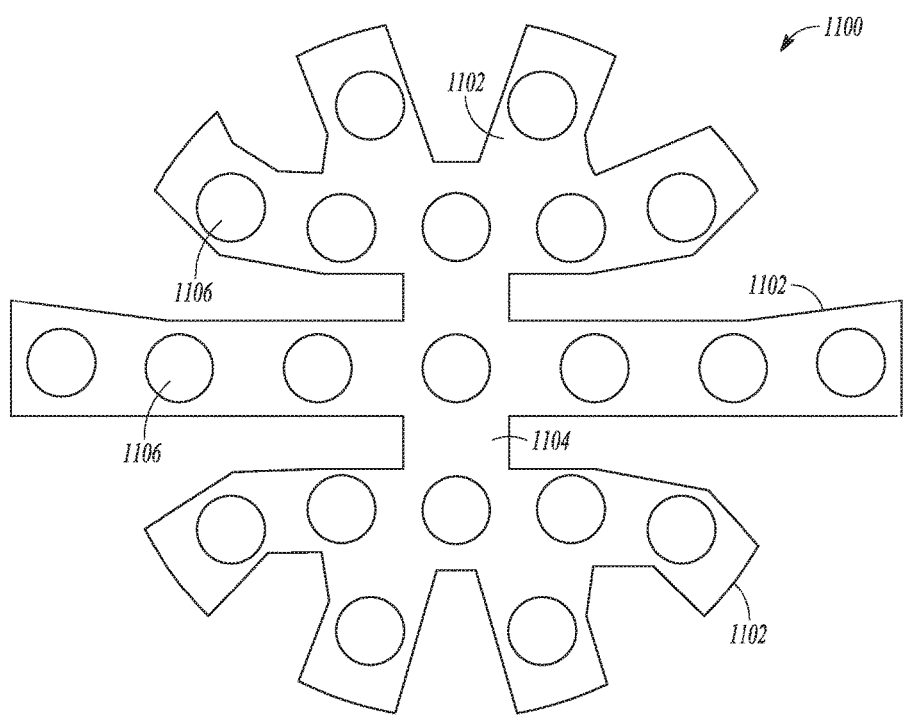
FIG. 15 illustrates an example of an EEG sensor assembly, in accordance with some embodiments.

FIG. 15 illustrates an example of an EEG sensor assembly 1100 that includes a plurality of branches 1102 that extend from a central trunk portion 1104. One or more connector interfaces can include a plurality of terminals coupled to traces corresponding to respective electrodes 1106. The EEG sensor assembly 1100 can include a shield plane on a surface opposite the electrodes 1106.

Figure 16:
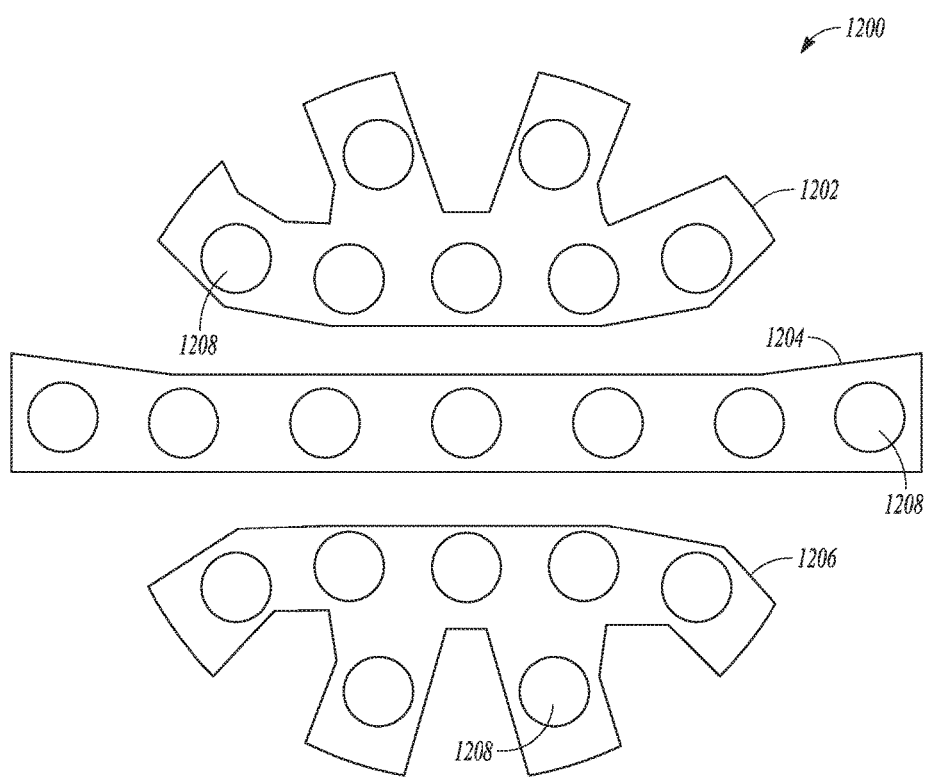
FIG. 16 illustrates an example of an EEG sensor assembly and an EEG sensor assembly strip, in accordance with some embodiments.

FIG. 16 illustrates an example of an EEG sensor assembly 1200 that includes three separate sub-assemblies. A frontal assembly 1202 can be secured to a patient's forehead. A coronal assembly 1204 can be secured over the top of a patient's head such that the ends of the coronal assembly are proximate to the patient's ears. A rear assembly 1206 can be secured to the back of a patient's head in a position proximate to the base of the spine. Each of the sub-assemblies can include a shield layer and a separate connector that interfaces each one of a plurality of electrodes 1208 in each sub-assembly to a shielded multi-connector cable that is coupled to an EEG recorder.

Figure 17:
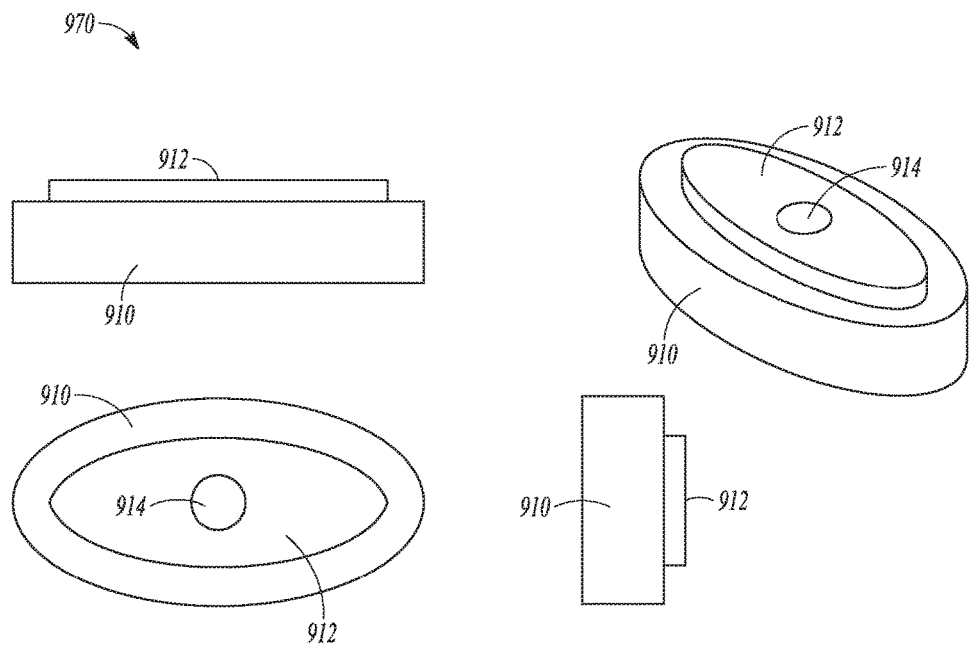
FIG. 17 illustrates an example dual-layer foam reservoir, in accordance with some embodiments.

FIG. 17 illustrates a dual-layer foam reservoir 970 that includes an inner layer 912 of low-density, high permeability foam, saturated with conductive gel. The inner layer 912 protrudes above an outer layer 910, thereby ensuring initial contact with the scalp during application. The surface area of the inner layer 912 can correspond to the area of the electrode (e.g., a silver-silver chloride disk) the inner layer 912 is disposed above.

In an example, the inner layer 912 can be pressure fitted inside the outer layer 910.

The outer layer 910 can include a foam that is not gelled and is of a higher density and lower permeability than the foam of the inner layer 912. The outer layer 910 can be affixed to an adhesive layer surrounding an electrode, thereby providing a rigid positioning of the pressure-fitted inner layer 912.

In example embodiments, the outer layer 910 can provide one or more of the following properties or advantages over alternative electrode assemblies. For example, increased electrode stability can be provided due to the mounting of the outer layer 910 on the adhesive layer and the outer layer's higher compression resistance. In an example, the outer layer 910 can provide a semi-permeable containment chamber for the gel-soaked inner layer 912 which keeps the gel concentrated in the target area. In addition, the outer layer 910 provides slow gel absorption, thereby keeping any excess gel contained and helping prevent bridging (e.g., electrical conduction or shorts between electrodes due to gel migration). In an example, the outer layer 910 provides the capability of re-gelling the inner layer 912 by providing expansion space for additional conductive gel to be added to the inner layer 912.

In an example, a re-gel cavity 914 can be formed though the center of the inner layer 912 that can align with a semi-perforated punch-through area in a flex circuit material (such as those discussed above), The semi-perforated punch-through area can allow a user (e.g., an EEG technician, or medical doctor) to penetrate the electrode assembly with a blunt needle and apply additional conductive gel to the electrode.

Figure 18:
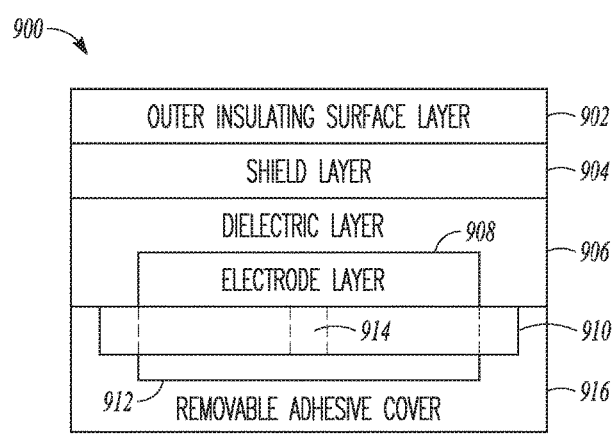
FIG. 18 illustrates a cross-sectional view of an example EEG sensor assembly with a dual-layer foam reservoir, in accordance with some embodiments.

FIG. 18 illustrates a cross-section view of a dual-layer foam reservoir 970 of FIG. 17 disposed on an EEG sensor strip 900. The EEG sensor strip 900 can include an outer insulating surface layer 902, a shield layer 904, a dielectric layer 906, and an electrode layer 908. The inner layer 912 of the dual-layer foam reservoir 970 can be affixed to the electrode layer 908 by adhering the outer layer 910 to a portion of the dielectric layer surrounding an individual electrode.

In an example, the re-gel cavity 914 formed at the center of the inner layer 912 can be accessed by inserting a blunt needle through the outer insulating surface layer 902, the shield layer 904, the dielectric layer 906, and the electrode layer 908. In an example, a removable adhesive cover 916 can be coupled to the dielectric layer 906 to protect the electrode layer 908. The removable adhesive cover 916 can be formed from a rigid or semi-rigid material that resists compression such that the dual-layer foam reservoir 970 is not compressed prior to the removal of the removable adhesive cover 916. By preventing the compression of the dual-layer foam reservoir 970 any conductive gel infused into the inner layer 912 is retained.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive.

For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An EEG sensor headset comprising:
a plurality of electrodes;
an elongated central strip defining one or more electrode-ports and including at least some of the plurality of electrodes and a first connector, the elongated central strip being sized to cover at least a portion of a center line from a nasal bridge to a spinal column of a patient, and being at least partially coated with a first adhesive on a patient side;
an anterior member including a first left wing and a first right wing, each of the first left wing and the first right wing extending from the central strip, the first left wing and the first right wing each having at least two of the plurality of electrodes, at least a portion of the anterior member being coated with the first adhesive on the patient side; a left-end portion of the first left wing and a right-end portion of the first right wing being coated with a second adhesive on the patient side;
a second anterior member including a second left wing and a second right wing each having an electrode of the plurality of the electrodes, each of the second left wing and the second right wing extending from the central strip; at least a portion of the second anterior member being coated with the first adhesive on the patient side, a left-end portion of the second left wing and a right-end portion of the second right wing being coated with the second adhesive on the patient side;
a right side member extending from the central strip and including an electrode of the plurality of electrodes, at least a portion of the right side member being coated with the first adhesive on the patient side;
a right contact member coupled to the right side member by a first lateral flex joint, the right contact member being coated with the second adhesive on the patient side;
a left side member extending from the central strip and including an electrode of the plurality of electrodes; a portion of the left side member being coated with the first adhesive on the patient side;
a left contact member coupled to the left side portion by a second lateral flex joint, the left contact member being coated with the second adhesive on the patient side;
a posterior member coated with the first adhesive on the patient side, the posterior member including:
a third left wing extending from the central strip and having at least three of the plurality of electrodes on the patient side, and an upper and a lower external adhesion location coated with the second adhesive on an outer side opposite the patient side, and
a third right wing extending from the central strip and having at least three of the plurality of electrodes on the patient side, and an upper and a lower external adhesion location coated with the second adhesive on the outer side;
the first connector disposed between the anterior member and the posterior member, the first connector electrically coupled to at least some of the plurality of electrodes by respective traces, the first connector including a terminal corresponding to respective electrodes; and
a shield plane including at least a portion coupled to the central strip, the shield plane coupled to a flexible outer substrate opposite the patient side, the flexible outer substrate providing a dielectric material disposed between the shield plane and the plurality of electrodes.

2. The EEG sensor headset of claim 1, comprising:
a lower ocular member having an electrode of the plurality of electrodes, coupled to the left contact member by a third lateral flex joint;

wherein the second lateral flex joint and the third lateral flex joint include at least one of the plurality of traces electrically coupling the electrode of the lower ocular member to the first connector.

3. The EEG sensor headset of claim 2, wherein the lower ocular member includes an adhesive opposite the electrode such that the lower ocular member can be adhered to the left contact member when the third lateral flex joint is bent at an angle of approximately 180 degrees.

4. The EEG sensor headset of claim 2, wherein the plurality of electrodes comprises at least nineteen electrodes.

5. The EEG sensor headset of claim 2, wherein the first lateral flex joint, the second lateral flex joint, and the third lateral flex joint have a width that is less than one-half a width of the elongated central strip.

6. The EEG sensor headset of claim 2, wherein the central strip is first central strip, and wherein the plurality of electrodes is a first plurality of electrodes, the headset further comprising:
an auxiliary sensor assembly including:
a second plurality of electrodes;
an elongated second central strip,
a pair of electrodes of the second plurality of electrodes configured to mate with a pair of the one or more electrode-ports of the elongated first central strip,
a left auxiliary wing extending from the second central strip and having an electrode of the second plurality of electrodes,
a right auxiliary wing extending from the second central strip and having an electrode of the second plurality of electrodes,
a left extension coupled to the left auxiliary wing by a fourth lateral flex joint,
a right extension coupled to the right auxiliary wing by a fifth lateral flex joint,
a left ear piece having an electrode of the second plurality of electrodes coupled to the left extension by a sixth lateral flex joint,
a right ear piece having an electrode of the second plurality of electrodes coupled to the right extension by a seventh lateral flex joint, and
a second connector electrically coupled to the second plurality of electrodes by a plurality of traces;
wherein the auxiliary sensor assembly defines a port disposed at a location corresponding to an electrode of the first plurality of the electrodes of the first central strip when the pair of electrodes of the second plurality of electrodes configured to mate with the pair of electrode-ports of the elongated first central strip are disposed in their respective ports.

7. The EEG sensor headset of claim 6, wherein the first plurality of electrodes comprises twenty-one electrodes arranged according to the International Standard 10-20 System.

8. The EEG sensor headset of claim 1, comprising:
a plurality of dual-layer foam reservoirs having an inner layer encircled at least in part by an annular outer layer, the inner layer in contact with a respective electrode.

9. The EEG sensor headset of claim 8, wherein the inner layer of the plurality of dual-layer foam reservoirs includes a conductive gel.

10. The EEG sensor headset of claim 8, further comprising a plurality of partial perforations in the flexible outer substrate, each partial perforation corresponding to a location of one of the electrodes such that a conductive gel can be applied through the flexible outer substrate to the inner layer.

11. The EEG sensor headset of claim 1, further comprising:
a second connector electrically coupled to a set of electrodes of the plurality of electrodes by a plurality of traces, the second connector including a terminal corresponding to a respective electrode of the set of the electrodes;
wherein the first connector is coupled to the electrodes of the plurality of electrodes that are excluded from the set of electrodes.

12. The EEG sensor headset of claim 1, wherein the second adhesive has a higher tack than the first adhesive.

13. The EEG sensor headset of claim 12, wherein the second adhesive has a tackiness twice as strong as the first adhesive, the first adhesive and the second adhesive both including a pressure-sensitive adhesive that does not cause skin irritation.

14. The EEG sensor headset of claim 1, further comprising:
a flexible circuit assembly including at least some of the traces;
foam reservoirs proximate to the respective electrodes, the foam reservoir including:
an outer band of foam having a first surface toward the flexible circuit assembly and an opposing second surface away from the flexible circuit assembly, the first surface being coupled to the flexible circuit assembly and extending about a respective electrode and defining a volume proximate the electrode; and
an inner region of foam, having a lower density and higher permeability than the outer band of foam, disposed in the volume and in contact with the electrode such that a portion of the inner volume of foam extends beyond the second surface of the outer band.

15. The sensor headset of claim 14, wherein the inner region of foam defines a central passageway from the electrode to an external surface of the inner region of foam.

16. The sensor headset of claim 15, wherein the flexible circuitry assembly and the electrode include a partial perforation coaxial to the central passageway of the inner region of foam.

17. The sensor headset of claim 14, wherein outer band of foam is annular and the inner region of foam is cylindrical.

18. The sensor headset of claim 14, wherein outer band of foam is polyethylene with a density of at least at least 100 pores per inch (PPI), and the inner region of foam has a density of at least 60 PPI.

19. The sensor headset of claim 14, wherein outer band of foam is polyethylene with a density of at least at least 90 pores per inch (PPI), and the inner region of foam has a density of at least 50 PPI.

* * * * *